(12) United States Patent
Galarza et al.

(10) Patent No.: US 11,529,410 B2
(45) Date of Patent: *Dec. 20, 2022

(54) UNIVERSAL VIRUS-LIKE PARTICLE (VLP) INFLUENZA VACCINES

(71) Applicant: TechnoVax, Inc., Elmsford, NY (US)

(72) Inventors: Jose M. Galarza, Elmsford, NY (US); George R. Martin, Elmsford, NY (US)

(73) Assignee: TECHNOVAX, INC., Elmsford, NY (US)

( * ) Notice: Subject to any disclaimer, the term of this patent is extended or adjusted under 35 U.S.C. 154(b) by 219 days.

This patent is subject to a terminal disclaimer.

(21) Appl. No.: 16/894,483

(22) Filed: Jun. 5, 2020

(65) Prior Publication Data

US 2020/0297836 A1  Sep. 24, 2020

Related U.S. Application Data

(63) Continuation of application No. 16/109,995, filed on Aug. 23, 2018, now Pat. No. 10,695,418, which is a continuation of application No. 15/148,699, filed on May 6, 2016, now Pat. No. 10,080,796, which is a continuation of application No. 12/932,217, filed on Feb. 18, 2011, now Pat. No. 9,352,031.

(60) Provisional application No. 61/305,759, filed on Feb. 18, 2010, provisional application No. 61/305,768, filed on Feb. 18, 2010.

(51) Int. Cl.
| *A61K 39/145* | (2006.01) |
| *A61K 39/12* | (2006.01) |
| *C12N 7/00* | (2006.01) |
| *A61K 39/00* | (2006.01) |

(52) U.S. Cl.
CPC ............ *A61K 39/145* (2013.01); *A61K 39/12* (2013.01); *C12N 7/00* (2013.01); *A61K 2039/5258* (2013.01); *C12N 2760/16023* (2013.01); *C12N 2760/16034* (2013.01); *C12N 2760/16134* (2013.01)

(58) Field of Classification Search
None
See application file for complete search history.

(56) References Cited

U.S. PATENT DOCUMENTS

| 9,352,031 | B2 * | 5/2016 | Galarza | .................. A61P 31/16 |
| 10,080,796 | B2 * | 9/2018 | Galarza | .................. A61K 39/12 |
| 2005/0186621 | A1 | 8/2005 | Galarza et al. | |
| 2006/0263804 | A1 | 11/2006 | Robinson et al. | |
| 2007/0184526 | A1 | 8/2007 | Smith et al. | |
| 2008/0031895 | A1 | 2/2008 | Galarza et al. | |
| 2008/0233150 | A1 | 9/2008 | Smith et al. | |
| 2009/0022762 | A1 | 1/2009 | Galarza et al. | |

(Continued)

OTHER PUBLICATIONS

Armstrong, et al. "The transmembrane domain of influenza hemagglutinin exhibits a stringent length requirement to support the hemifusion to fusion transition." The Journal of cell biology 151.2 (2000): 425-437.

(Continued)

*Primary Examiner* — Michelle S Horning
(74) *Attorney, Agent, or Firm* — Leason Ellis LLP

(57) ABSTRACT

Described herein are influenza virus-like particles (VLPs) that display on truncated, re-engineered or remodeled HA molecules on their surface. Also described are methods of making and using these VLPs.

21 Claims, 14 Drawing Sheets

Specification includes a Sequence Listing.

(56) References Cited

U.S. PATENT DOCUMENTS

2010/0047266 A1   2/2010   Haynes
2010/0172934 A1   7/2010   Krenn et al.
2010/0297174 A1  11/2010  Garcia-Sastre et al.

OTHER PUBLICATIONS

Galarza, et al. "Virus-like particle (VLP) vaccine conferred complete protection against a lethal influenza virus challenge." Viral immunology 18.1 (2005): 244-251.

Flandorfer, et al. "Chimeric influenza A viruses with a functional influenza B virus neuraminidase or hemagglutinin." Journal of virology 77.17 (2003): 9116-9123.

Ha, et al. "H5 avian and H9 swine influenza virus haemagglutinin structures: possible origin of influenza subtypes." The EMBO journal 21.5 (2002): 865-875.

Kang, et al. "Influenza virus-like particles as pandemic vaccines." Vaccines for Pandemic Influenza. Springer, Bedin, Heidelberg, 2009. 269-289.

Latham et al. "Formation of wild-type and chimeric influenza virus-like particles following simultaneous expression of only four structural proteins." Journal of Virology 75.13 (2001): 6154-6165.

Sagawa et al. "The immunological activity of a deletion mutant of influenza virus haemagglutinin lacking the globular region." Journal of General Virology 77.7 (1996): 1483-1487.

Sui et al. "Structural and functional bases for broad-spectrum neutralization of avian and human influenza A viruses." Nature Structural & Molecular Biology 16.3 (2009): 265-273.

Takeda et al. "Influenza virus hemagglutinin concentrates in lipid raft microdomains for efficient viral fusion." Proceedings of the National Academy of Sciences 100.25 (2003): 14610-14617.

Watanabe et al. "Exploitation of nucleic acid packaging signals to generate a novel influenza virus-based vector stably expressing two foreign genes." Journal of Virology 77.19 (2003): 10575-10583.

Webby et al. "Responsiveness to a pandemic alert: use of reverse genetics for rapid development of influenza vaccines." The Lancet 363.9415 (2004): 1099-1103.

\* cited by examiner

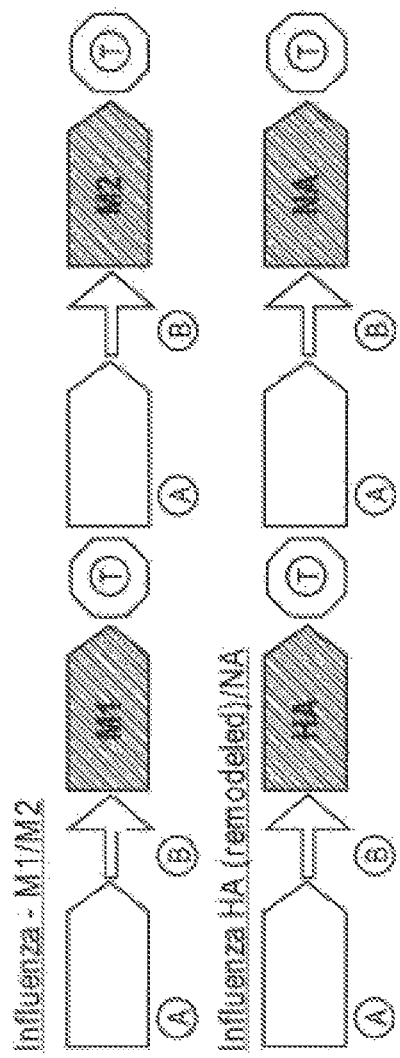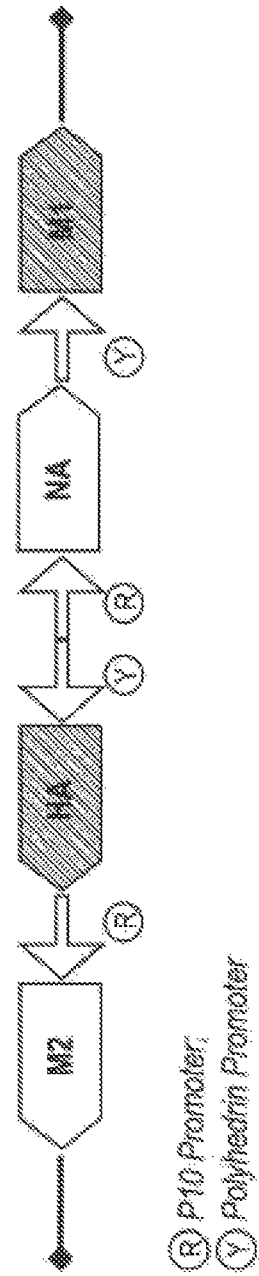

Transient Transfection for Influenza-VLP Production

Transfection
by electroporation or lipofectamine transfection.

| M1 | M2 | + | HA Remodeled 1-5 |
or
| M1 | M2 | + | NA | HA Remodeled 1-5 |

OR

| Thogoto M | M2 | + | HA Remodeled 1-5 |
or
| Thogoto M | M2 | + | NA | HA Remodeled 1-5 |

Flu-VLP production cells with M1/M2+HA+NA or Thogoto M+M2+HA+NA

Transient VLP-Production

FLU-VLPs

FIG. 7A

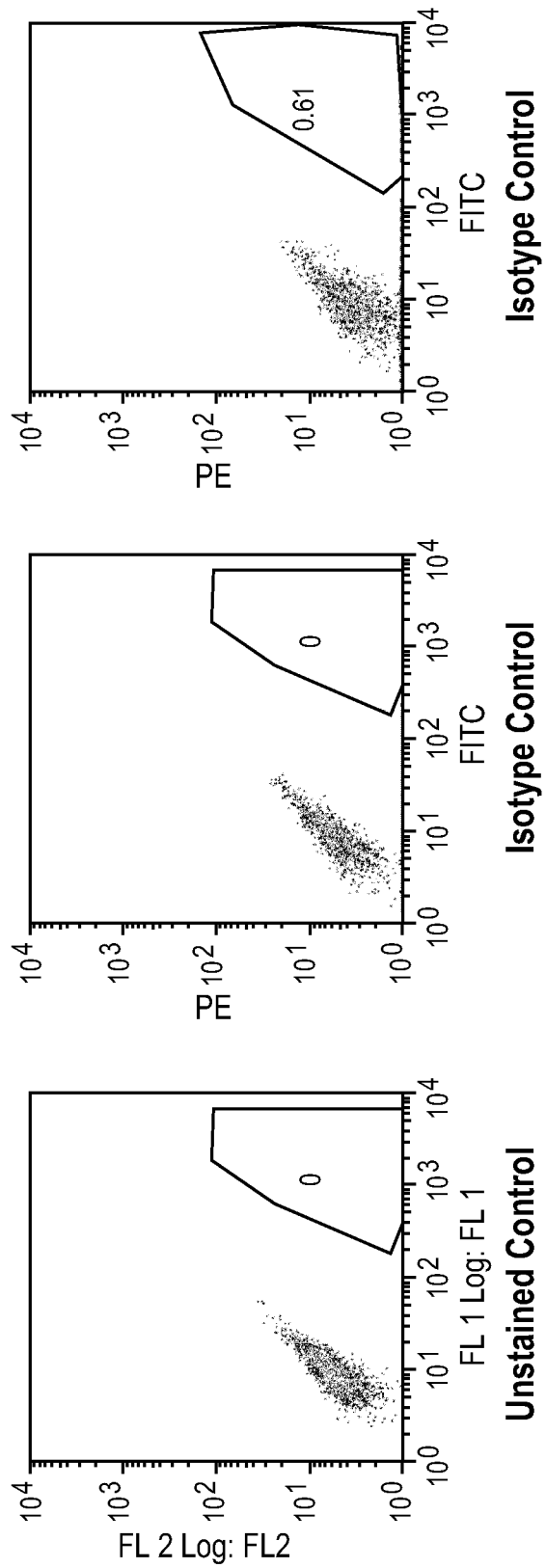

Production of Flu VLPs with Remodeled HA Molecules in CHO Cells.

MW kDa: 115, 82, 64, 49, 37, 26, 19, 15, 6

Lanes: (1) (2) (3) (4) (5) (6)

Bands labeled: $HA_0$, $HA_1$, $HA_2$, M1, M2

(1) Virus Control
(2) Negative Control CHO cells
(3) 5TA Cell Lysate
(4) 5TA 38p
(5) 3TA Cell Lysate
(6) 3TA 38p Western Blot analysis of cell lysates and concentrated/purified culture supernatant (38p) of CHO cells transfected with vectors M1/M2 plus NA/HA remodeled -5TA and 3TA.

FIG. 10

SEQUENCE LISTING

<160> NUMBER OF SEQ ID NOS: 13

<210> SEQ ID NO 1
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggagaaaa tagtgcttct ttttgcaata gtcagtcttg ttaaaagtga tcagatttgc      60
attggttaca ggatggagtt cttctggaca attttaaagc cgaatgatgc aatcaacttc     120
gagagtaatg gaaatttcat tgctccagaa tatgcataca aaattgtcaa gaaaggggac     180
tcaacaatta tgaaaagtga attggaatat ggtaacggaa acaccaagtg tcaaactcca     240 atggggggcga taaactctag catgccattc cacaatatac ccctctcac  cattggggaa     300 tgccccaaat atgtgaaatc aaacagatta gtccttgcga ctgggctcag aaatagccct     360
caaagagaga gaagaagaaa aaagagagga ttatttggag ctatagcagg ttttatagag     420
ggaggatggc agggaatggt agatggttgg tatgggtacc accatagcaa tgagcagggg     480
agtgggtacg ctgcagacaa agaatccact caaaaggcaa tagatggagt caccaataag     540
gtcaactcga tcattgacaa aatgaacact cagtttgagg ccgttggaag ggaatttaac     600
aacttagaaa ggagaataga gaatttaaac aagaagatgg aagacgggtt cctagatgtc     660
tggacttata atgctgaact tctggttctc atggaaaatg agagaactct agactttcat     720
gactcaaatg tcaagaacct ttacgacaag gtccgactac agcttaggga taatgcaaag     780
gagctgggta acggttgttt cgagttctat cataaatgtg ataatgaatg tatggaaagt     840
gtaagaaatg gaacgtatga ctacccgcag tattcagaag aagcgagact aaaaagagag     900
gaaataagtg gagtaaaatt ggaatcaata ggaatttacc aaatactgtc aatttattct     960
acagtggcga gttccctagc actggcaatc atggtagctg gtctatcctt atggatgtgc    1020
tccaatgggt cgttacaatg cagaatttgc atttaa                              1056
```

<210> SEQ ID NO 2
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Glu Lys Ile Val Leu Leu Phe Ala Ile Val Ser Leu Val Lys Ser
1               5                   10                  15

Asp Gln Ile Cys Ile Gly Tyr Arg Met Glu Phe Phe Trp Thr Ile Leu
            20                  25                  30

Lys Pro Asn Asp Ala Ile Asn Phe Glu Ser Asn Gly Asn Phe Ile Ala
                35                  40                  45

Pro Glu Tyr Ala Tyr Lys Ile Val Lys Lys Gly Asp Ser Thr Ile Met
    50                  55                  60

Lys Ser Glu Leu Glu Tyr Gly Asn Gly Asn Thr Lys Cys Gln Thr Pro
65                  70                  75                  80

Met Gly Ala Ile Asn Ser Ser Met Pro Phe His Asn Ile His Pro Leu
                85                  90                  95

Thr Ile Gly Glu Cys Pro Lys Tyr Val Lys Ser Asn Arg Leu Val Leu
            100                 105                 110

Ala Thr Gly Leu Arg Asn Ser Pro Gln Arg Glu Arg Arg Lys Lys
            115                 120                 125

Arg Gly Leu Phe Gly Ala Ile Ala Gly Phe Ile Glu Gly Gly Trp Gln
    130                 135                 140

Gly Met Val Asp Gly Trp Tyr Gly Tyr His His Ser Asn Glu Gln Gly
145                 150                 155                 160

Ser Gly Tyr Ala Ala Asp Lys Glu Ser Thr Gln Lys Ala Ile Asp Gly
                165                 170                 175

Val Thr Asn Lys Val Asn Ser Ile Ile Asp Lys Met Asn Thr Gln Phe
                180                 185                 190

Glu Ala Val Gly Arg Glu Phe Asn Asn Leu Glu Arg Arg Ile Glu Asn
            195                 200                 205

Leu Asn Lys Lys Met Glu Asp Gly Phe Leu Asp Val Trp Thr Tyr Asn
210                 215                 220

Ala Glu Leu Leu Val Leu Met Glu Asn Glu Arg Thr Leu Asp Phe His
225                 230                 235                 240

Asp Ser Asn Val Lys Asn Leu Tyr Asp Lys Val Arg Leu Gln Leu Arg
                245                 250                 255

Asp Asn Ala Lys Glu Leu Gly Asn Gly Cys Phe Glu Phe Tyr His Lys
                260                 265                 270

Cys Asp Asn Glu Cys Met Glu Ser Val Arg Asn Gly Thr Tyr Asp Tyr
    275                 280                 285

Pro Gln Tyr Ser Glu Glu Ala Arg Leu Lys Arg Glu Glu Ile Ser Gly
    290                 295                 300

Val Lys Leu Glu Ser Ile Gly Ile Tyr Gln Ile Leu Ser Ile Tyr Ser
305                 310                 315                 320

Thr Val Ala Ser Ser Leu Ala Leu Ala Ile Met Val Ala Gly Leu Ser
                325                 330                 335

Leu Trp Met Cys Ser Asn Gly Ser Leu Gln Cys Arg Ile Cys Ile
                340                 345                 350

<210> SEQ ID NO 3
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggagaaaa tagtgcttct ttttgcaata gtcagtcttg ttaaaagtga tcagatttgc    60
```

-continued

```
attggttacc atgcaaacaa ctcgacagag caggttgaca caataatgga aaagaacgtt    120
actgttacac atgcccaaga catactggaa aagaaacaca acgggaagct ctgcgatcta    180
gatggagtga agcctaggat ggagttcttc tggacaattt aaagccgaa tgatgcaatc     240 aacttcgaga gtaatggaaa tttcattgct ccagaatatg catacaaaat tgtcaagaaa    300
ggggactcaa caattatgaa aagtgaattg gaatatggta actgcaacac caagtgtcaa    360
actccaatgg gggcgataaa ctctagcatg ccattccaca atatacaccc tctcaccatt    420
ggggaatgcc ccaaatatgt gaaatcaaac agattagtcc ttgcgactgg gctcagaaat    480
agccctcaaa gagagagaag aagaaaaaag agaggattat ttggagctat agcaggtttt    540
atagagggag gatggcaggg aatggtagat ggttggtatg ggtaccacca tagcaatgag    600 cagggagtg ggtacgctgc agacaaagaa tccactcaaa aggcaataga tggagtcacc     660
aataaggtca actcgatcat tgacaaaatg aacactcagt ttgaggccgt tggaagggaa    720
tttaacaact agaaaggag aatagagaat ttaaacaaga gatggaaga cgggttccta      780 gatgtctgga cttataatgc tgaacttctg gttctcatgg aaaatgagag aactctagac    840
tttcatgact caaatgtcaa gaacctttac gacaaggtcc gactacagct tagggataat    900
gcaaaggagc tgggtaacgg ttgtttcgag ttctatcata aatgtgataa tgaatgtatg    960
gaaagtgtaa gaaatggaac gtatgactac ccgcagtatt cagaagaagc gagactaaaa    1020
agagaggaaa taagtggagt aaaattggaa tcaataggaa tttaccaaat actgtcaatt    1080
tattctacag tggcgagttc cctagcactg gcaatcatgg tagctggtct atccttatgg    1140
atgtgctcca atgggtcgtt acaatgcaga atttgcattt aa                      1182
```

<210> SEQ ID NO 4
<211> LENGTH: 393
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 4

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Arg Met Glu Phe Phe Trp Thr Ile Leu Lys Pro Asn Asp Ala Ile
65                  70                  75                  80

Asn Phe Glu Ser Asn Gly Asn Phe Ile Ala Pro Glu Tyr Ala Tyr Lys
                85                  90                  95

Ile Val Lys Lys Gly Asp Ser Thr Ile Met Lys Ser Glu Leu Glu Tyr
            100                 105                 110

Gly Asn Cys Asn Thr Lys Cys Gln Thr Pro Met Gly Ala Ile Asn Ser
        115                 120                 125

Ser Met Pro Phe His Asn Ile His Pro Leu Thr Ile Gly Glu Cys Pro
    130                 135                 140

Lys Tyr Val Lys Ser Asn Arg Leu Val Leu Ala Thr Gly Leu Arg Asn
145                 150                 155                 160
```

Ser Pro Gln Arg Glu Arg Arg Lys Lys Arg Gly Leu Phe Gly Ala
            165                 170                 175

Ile Ala Gly Phe Ile Glu Gly Gly Trp Gln Gly Met Val Asp Gly Trp
        180                 185                 190

Tyr Gly Tyr His His Ser Asn Glu Gln Gly Ser Gly Tyr Ala Ala Asp
            195                 200                 205

Lys Glu Ser Thr Gln Lys Ala Ile Asp Gly Val Thr Asn Lys Val Asn
        210                 215                 220

Ser Ile Ile Asp Lys Met Asn Thr Gln Phe Glu Ala Val Gly Arg Glu
225                 230                 235                 240

Phe Asn Asn Leu Glu Arg Arg Ile Glu Asn Leu Asn Lys Lys Met Glu
            245                 250                 255

Asp Gly Phe Leu Asp Val Trp Thr Tyr Asn Ala Glu Leu Leu Val Leu
        260                 265                 270

Met Glu Asn Glu Arg Thr Leu Asp Phe His Asp Ser Asn Val Lys Asn
        275                 280                 285

Leu Tyr Asp Lys Val Arg Leu Gln Leu Arg Asp Asn Ala Lys Glu Leu
        290                 295                 300

Gly Asn Gly Cys Phe Glu Phe Tyr His Lys Cys Asp Asn Glu Cys Met
305                 310                 315                 320

Glu Ser Val Arg Asn Gly Thr Tyr Asp Tyr Pro Gln Tyr Ser Glu Glu
                325                 330                 335

Ala Arg Leu Lys Arg Glu Glu Ile Ser Gly Val Lys Leu Glu Ser Ile
            340                 345                 350

Gly Ile Tyr Gln Ile Leu Ser Ile Tyr Ser Thr Val Ala Ser Ser Leu
        355                 360                 365

Ala Leu Ala Ile Met Val Ala Gly Leu Ser Leu Trp Met Cys Ser Asn
370                 375                 380

Gly Ser Leu Gln Cys Arg Ile Cys Ile
385                 390

<210> SEQ ID NO 5
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggagaaaa tagtgcttct ttttgcaata gtcagtcttg ttaaaagtga tcagatttgc     60
attggttacc atgcaaacaa ctcgacagag caggttgaca caataatgga aaagaacgtt    120
actgttacac atgcccaaga catactggaa aagaaacaca acgggaagct ctgcgatcta    180
gatggagtga agcctgacat aggaccagga aaggtaggat acggaccagg aatgaaaagt    240
gaattggaat atggtaactg caacaccaag tgtcaaactc aatggggggc gataaactct    300
agcatgccat tccacaatat acaccctctc accattgggg aatgccccaa atatgtgaaa    360
tcaaacagat tagtccttgc gactgggctc agaaatagcc tcaaagaga gagaagaaga    420 aaaagagag gattatttgg agctatagca ggttttatag gggaggatg gcagggaatg    480 gtagatggtt ggtatgggta ccaccatagc aatgagcagg ggagtgggta cgctgcagac    540
aaagaatcca ctcaaaaggc aatagatgga gtcaccaata aggtcaactc gatcattgac    600
aaaatgaaca ctcagtttga ggccgacgga agggaattta caacggaga aggagaata    660 gagaatttaa acaagaagat ggaagacggg ttcctagatg tctggactta taatgctgaa    720

```
cttctggttc tcatggaaaa tgagagaact ctagactttc atgactcaaa tgtcaagaac    780
ctttacgaca aggtccgact acagcttagg gataatgcaa aggagctggg taacggttgt    840
ttcgagttct atcataaatg tgataatgaa tgtatggaaa gtgtaagaaa tggaacgtat    900 gactaccccgc agtattcaga agaagcgaga ctaaaaagag aggaaataag tggagtaaaa    960
ttggaatcaa taggaattta ccaaatactg tcaatttatt ctacagtggc gagttcccta   1020
gcactggcaa tcatggtagc tggtctatcc ttatggatgt gctccaatgg gtcgttacaa   1080
tgcagaattt gcatttaa                                                1098
```

<210> SEQ ID NO 6
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Asp Ile Gly Pro Gly Lys Val Gly Tyr Gly Pro Gly Met Lys Ser
65                  70                  75                  80

Glu Leu Glu Tyr Gly Asn Cys Asn Thr Lys Cys Gln Thr Pro Met Gly
                85                  90                  95

Ala Ile Asn Ser Ser Met Pro Phe His Asn Ile His Pro Leu Thr Ile
            100                 105                 110

Gly Glu Cys Pro Lys Tyr Val Lys Ser Asn Arg Leu Val Leu Ala Thr
        115                 120                 125

Gly Leu Arg Asn Ser Pro Gln Arg Glu Arg Arg Lys Lys Arg Gly
    130                 135                 140

Leu Phe Gly Ala Ile Ala Gly Phe Ile Glu Gly Gly Trp Gln Gly Met
145                 150                 155                 160

Val Asp Gly Trp Tyr Gly Tyr His His Ser Asn Glu Gln Gly Ser Gly
                165                 170                 175

Tyr Ala Ala Asp Lys Glu Ser Thr Gln Lys Ala Ile Asp Gly Val Thr
            180                 185                 190

Asn Lys Val Asn Ser Ile Ile Asp Lys Met Asn Thr Gln Phe Glu Ala
        195                 200                 205

Asp Gly Arg Glu Phe Asn Asn Gly Glu Arg Arg Ile Glu Asn Leu Asn
    210                 215                 220

Lys Lys Met Glu Asp Gly Phe Leu Asp Val Trp Thr Tyr Asn Ala Glu
225                 230                 235                 240

Leu Leu Val Leu Met Glu Asn Glu Arg Thr Leu Asp Phe His Asp Ser
                245                 250                 255

Asn Val Lys Asn Leu Tyr Asp Lys Val Arg Leu Gln Leu Arg Asp Asn
            260                 265                 270

Ala Lys Glu Leu Gly Asn Gly Cys Phe Glu Phe Tyr His Lys Cys Asp
        275                 280                 285
```

```
Asn Glu Cys Met Glu Ser Val Arg Asn Gly Thr Tyr Asp Tyr Pro Gln
        290                 295                 300

Tyr Ser Glu Glu Ala Arg Leu Lys Arg Glu Glu Ile Ser Gly Val Lys
305                 310                 315                 320

Leu Glu Ser Ile Gly Ile Tyr Gln Ile Leu Ser Ile Tyr Ser Thr Val
                325                 330                 335

Ala Ser Ser Leu Ala Leu Ala Ile Met Val Ala Gly Leu Ser Leu Trp
            340                 345                 350

Met Cys Ser Asn Gly Ser Leu Gln Cys Arg Ile Cys Ile
            355                 360                 365

<210> SEQ ID NO 7
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggagaaaa tagtgcttct ttttgcaata gtcagtcttg ttaaaagtgg attatttgga      60
gctatagcag gttttataga gggaggatgg cagggaatgg tagatggttg gtatgggtac     120
caccatagca atgagcaggg gagtgggtac gctgcagaca agaatccact caaaaggca      180 atagatggag tcaccaataa ggtcaactcg atcattgaca aaatgaacac tcagtttgag     240
gccgttggaa gggaatttaa caacttagaa aggagaatag agaatttaaa caagaagatg     300
gaagacgggt tcctagatgt ctggacttat aatgctgaac ttctggttct catggaaaat     360
gagagaactc tagactttca tgactcaaat gtcaagaacc tttacgacaa ggtccgacta     420
cagcttaggg ataatgcaaa ggagctgggt aacggttgtt tcgagttcta tcataaatgt     480
gataatgaat gtatggaaag tgtaagaaat ggaacgtatg actacccgca gtattcagaa     540
gaagcgagac taaaaagaga ggaaataagt ggagtaaaat tggaatcaat aggaatttac     600
caaatactgt caatttattc tacagtggcg agttccctag cactggcaat catggtagct     660
ggtctatcct tatggatgtg ctccaatggg tcgttacaat gcagaatttg catttaa       717

<210> SEQ ID NO 8
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Lys Ile Val Leu Leu Phe Ala Ile Val Ser Leu Val Lys Ser
1               5                   10                  15

Gly Leu Phe Gly Ala Ile Ala Gly Phe Ile Glu Gly Gly Trp Gln Gly
                20                  25                  30

Met Val Asp Gly Trp Tyr Gly Tyr His His Ser Asn Glu Gln Gly Ser
            35                  40                  45

Gly Tyr Ala Ala Asp Lys Glu Ser Thr Gln Lys Ala Ile Asp Gly Val
        50                  55                  60

Thr Asn Lys Val Asn Ser Ile Ile Asp Lys Met Asn Thr Gln Phe Glu
65                  70                  75                  80

Ala Val Gly Arg Glu Phe Asn Asn Leu Glu Arg Arg Ile Glu Asn Leu
                85                  90                  95
```

```
Asn Lys Lys Met Glu Asp Gly Phe Leu Asp Val Trp Thr Tyr Asn Ala
            100                 105                 110
Glu Leu Leu Val Leu Met Glu Asn Glu Arg Thr Leu Asp Phe His Asp
        115                 120                 125
Ser Asn Val Lys Asn Leu Tyr Asp Lys Val Arg Leu Gln Leu Arg Asp
    130                 135                 140
Asn Ala Lys Glu Leu Gly Asn Gly Cys Phe Glu Phe Tyr His Lys Cys
145                 150                 155                 160
Asp Asn Glu Cys Met Glu Ser Val Arg Asn Gly Thr Tyr Asp Tyr Pro
                165                 170                 175
Gln Tyr Ser Glu Glu Ala Arg Leu Lys Arg Glu Glu Ile Ser Gly Val
            180                 185                 190
Lys Leu Glu Ser Ile Gly Ile Tyr Gln Ile Leu Ser Ile Tyr Ser Thr
        195                 200                 205
Val Ala Ser Ser Leu Ala Leu Ala Ile Met Val Ala Gly Leu Ser Leu
    210                 215                 220
Trp Met Cys Ser Asn Gly Ser Leu Gln Cys Arg Ile Cys Ile
225                 230                 235
```

<210> SEQ ID NO 9
<211> LENGTH: 1767
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | | |
|---|---|---|
| atggagaaaa tagtgcttct ttttgcaata gtcagtcttg ttaaaagtga tcagatttgc | 60 |
| attggttacc atgcaaacaa ctcgacagag caggttgaca caataatgga aagaacgtt | 120 |
| actgttacac atgcccaaga catactggaa aagaaacaca acgggaagct ctgcgatcta | 180 |
| gatggagtga agcctccaca gagagaaaga agaagaaaga agagactaat tttgagagat | 240 |
| tgtagcgtag ctggatggct cctcggaaac ccaatgtgtg acgaattcat caatgtgccg | 300 |
| gaatggtctt acatagtgga aaggccaat ccagtcaatg acctctgtta cccaggggat | 360 |
| ttcaatgact atgaagaatt gaaacaccta ttgcagcagaa taaaccattt tgagaaaatt | 420 |
| cagatcatcc ccaaaagttc ttggtccagt catgaagcct cattagggt gagctcagca | 480 |
| tgtccatacc agggaaagtc ctcctttttc agaaatgtgg tatggcttat caaaagaac | 540 |
| agtacatacc caacaataaa gaggagctac aataatacca accaagaaga tcttttggta | 600 |
| ctgtggggga ttcaccatcc taatgatgcg gcagagcaga caagctcta tcaaaaccca | 660 |
| accacctata tttccgttgg gacatcaaca ctaaaccaga gattggtacc aagaatagct | 720 |
| actagatcca aagtaaacgg gcaaagtgga aggatggagt tcttctggac aattttaaag | 780 |
| ccgaatgatg caatcaactt cgagagtaat ggaaatttca ttgctccaga atatgcatac | 840 |
| aaaattgtca agaaggggga ctcaacaatt ccacagagag aagaagaag aagaagaga | 900 |
| atgaaagtg aattggaata tggtaactgc aacaccaagt gtcaaactcc aatggggcg | 960 |
| ataaactcta gcatgccatt ccacaatata caccctctca ccattgggga atgccccaaa | 1020 |
| tatgtgaaat caaacagatt agtccttgcg actgggctca gaaatagccc tcaaagagag | 1080 |
| agaagaagaa agaagagagg attatttgga gctatagcag gttttataga gggaggatgg | 1140 |
| cagggaatgg tagatggttg gtatgggtac accatagca atgagcaggg gagtgggtac | 1200 |

```
gctgcagaca aagaatccac tcaaaaggca atagatggag tcaccaataa ggtcaactcg   1260
atcattgaca aaatgaacac tcagtttgag gccgttggaa gggaatttaa caacttagaa   1320
aggagaatag agaatttaaa caagaagatg gaagacgggt tcctagatgt ctggacttat   1380
aatgctgaac ttctggttct catggaaaat gagagaactc tagactttca tgactcaaat   1440
gtcaagaacc tttacgacaa ggtccgacta cagcttaggg ataatgcaaa ggagctgggt   1500
aacggttgtt tcgagttcta tcataaatgt gataatgaat gtatggaaag tgtaagaaat   1560
ggaacgtatg actacccgca gtattcagaa gaagcgagac taaaaagaga ggaaataagt   1620
ggagtaaaat tggaatcaat aggaatttac caaatactgt caatttattc tacagtggcg   1680
agttccctag cactggcaat catggtagct ggtctatcct tatggatgtg ctccaatggg   1740
tcgttacaat gcagaatttg catttaa                                      1767
```

<210> SEQ ID NO 10
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Pro Gln Arg Glu Arg Arg Lys Lys Arg Leu Ile Leu Arg Asp
65                  70                  75                  80

Cys Ser Val Ala Gly Trp Leu Leu Gly Asn Pro Met Cys Asp Glu Phe
                85                  90                  95

Ile Asn Val Pro Glu Trp Ser Tyr Ile Val Glu Lys Ala Asn Pro Val
            100                 105                 110

Asn Asp Leu Cys Tyr Pro Gly Asp Phe Asn Asp Tyr Glu Glu Leu Lys
        115                 120                 125

His Leu Leu Ser Arg Ile Asn His Phe Glu Lys Ile Gln Ile Ile Pro
    130                 135                 140

Lys Ser Ser Trp Ser Ser His Glu Ala Ser Leu Gly Val Ser Ser Ala
145                 150                 155                 160

Cys Pro Tyr Gln Gly Lys Ser Ser Phe Phe Arg Asn Val Val Trp Leu
                165                 170                 175

Ile Lys Lys Asn Ser Thr Tyr Pro Thr Ile Lys Arg Ser Tyr Asn Asn
            180                 185                 190

Thr Asn Gln Glu Asp Leu Leu Val Leu Trp Gly Ile His His Pro Asn
        195                 200                 205

Asp Ala Ala Glu Gln Thr Lys Leu Tyr Gln Asn Pro Thr Thr Tyr Ile
    210                 215                 220

Ser Val Gly Thr Ser Thr Leu Asn Gln Arg Leu Val Pro Arg Ile Ala
225                 230                 235                 240

Thr Arg Ser Lys Val Asn Gly Gln Ser Gly Arg Met Glu Phe Phe Trp
                245                 250                 255
```

```
Thr Ile Leu Lys Pro Asn Asp Ala Ile Asn Phe Glu Ser Asn Gly Asn
            260                 265                 270

Phe Ile Ala Pro Glu Tyr Ala Tyr Lys Ile Val Lys Lys Gly Asp Ser
        275                 280                 285

Thr Ile Pro Gln Arg Glu Arg Arg Lys Lys Arg Met Lys Ser Glu
    290                 295                 300

Leu Glu Tyr Gly Asn Cys Asn Thr Lys Cys Gln Thr Pro Met Gly Ala
305                 310                 315                 320

Ile Asn Ser Ser Met Pro Phe His Asn Ile His Pro Leu Thr Ile Gly
                325                 330                 335

Glu Cys Pro Lys Tyr Val Lys Ser Asn Arg Leu Val Leu Ala Thr Gly
            340                 345                 350

Leu Arg Asn Ser Pro Gln Arg Glu Arg Arg Lys Lys Arg Gly Leu
        355                 360                 365

Phe Gly Ala Ile Ala Gly Phe Ile Glu Gly Gly Trp Gln Gly Met Val
    370                 375                 380

Asp Gly Trp Tyr Gly Tyr His His Ser Asn Glu Gln Gly Ser Gly Tyr
385                 390                 395                 400

Ala Ala Asp Lys Glu Ser Thr Gln Lys Ala Ile Asp Gly Val Thr Asn
            405                 410                 415

Lys Val Asn Ser Ile Ile Asp Lys Met Asn Thr Gln Phe Glu Ala Val
        420                 425                 430

Gly Arg Glu Phe Asn Asn Leu Glu Arg Arg Ile Glu Asn Leu Asn Lys
    435                 440                 445

Lys Met Glu Asp Gly Phe Leu Asp Val Trp Thr Tyr Asn Ala Glu Leu
450                 455                 460

Leu Val Leu Met Glu Asn Glu Arg Thr Leu Asp Phe His Asp Ser Asn
465                 470                 475                 480

Val Lys Asn Leu Tyr Asp Lys Val Arg Leu Gln Leu Arg Asp Asn Ala
            485                 490                 495

Lys Glu Leu Gly Asn Gly Cys Phe Glu Phe Tyr His Lys Cys Asp Asn
        500                 505                 510

Glu Cys Met Glu Ser Val Arg Asn Gly Thr Tyr Asp Tyr Pro Gln Tyr
    515                 520                 525

Ser Glu Glu Ala Arg Leu Lys Arg Glu Glu Ile Ser Gly Val Lys Leu
530                 535                 540

Glu Ser Ile Gly Ile Tyr Gln Ile Leu Ser Ile Tyr Ser Thr Val Ala
545                 550                 555                 560

Ser Ser Leu Ala Leu Ala Ile Met Val Ala Gly Leu Ser Leu Trp Met
            565                 570                 575

Cys Ser Asn Gly Ser Leu Gln Cys Arg Ile Cys Ile
        580                 585

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ile Gly Pro Gly Lys Val Gly Tyr Gly Pro Gly
1               5                   10

<210> SEQ ID NO 12
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Gln Arg Glu Arg Arg Arg Lys Lys Arg
1               5                   10

<210> SEQ ID NO 13
<211> LENGTH: 568
<212> TYPE: PRT
<213> ORGANISM: Influenza A virus

<400> SEQUENCE: 13

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320
```

-continued

```
Tyr Val Lys Ser Asn Arg Leu Val Leu Ala Thr Gly Leu Arg Asn Ser
            325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565
```

UNIVERSAL VIRUS-LIKE PARTICLE (VLP) INFLUENZA VACCINES

CROSS REFERENCE TO RELATED APPLICATIONS

This application is a continuation of U.S. patent application Ser. No. 16/109,995 filed on Aug. 23, 2018, which is a continuation of U.S. patent application Ser. No. 15/148,699 filed on May 6, 2016, now U.S. Pat. No. 10,080,796 issued on Sep. 25, 2018, which is a continuation of U.S. patent application Ser. No. 12/932,217 filed on Feb. 18, 2011, now U.S. Pat. No. 9,352,031 issued on May 31, 2016, which claims priority from U.S. Provisional Application Nos. 61/305,768 and 61/305,759, both filed Feb. 18, 2010, all of which are hereby incorporated by reference in their respective entireties.

STATEMENT AS TO FEDERALLY SPONSORED RESEARCH

Not Applicable.

TECHNICAL FIELD

Virus-like particles (VLPs) comprising antigenic influenza proteins are described, as are methods for making and using these VLPs.

BACKGROUND

Influenza viruses (type A, B, and C) are the causative agents of respiratory infections in humans and other mammalian and avian species. Unique biological and epidemiological characteristics in the virus life cycle drive a rapid antigenic evolution and continuous emergence of new virus strains, particularly of the type A virus. This continuous emergence of antigenic variants allows for seasonal influenza epidemics and at irregular intervals global pandemics. Annual influenza epidemics are associated with approximately 36,000 deaths in the United States alone and more than 250,000 fatalities worldwide each year while causing enormous health and economical burdens. Pandemic influenza poses a serious threat to human health and such global events as the 1918 pandemic caused an estimated 50 millions death and devastating socio-economical effects.

Influenza viruses have a single stranded, segmented RNA genome and are members of the Orthomyxoviridae family. Influenza A viruses display two major glycoproteins on the surface of the virion particle, the hemagglutinin (HA) and the neuraminidase (NA) and based on the antigenic properties of these two molecules they are classified into 16 HA subtypes (H1-H16) and 9 NA subtypes (N1-N9). The predominant immune response following influenza infection targets the surface glycoprotein HA and NA. Antibodies against the HA are able to block virus binding to the cell surface receptor and prevent virus entry and infection. Over time, however, this response is rendered ineffective and unable to protect against emerging antigenic variants resulting from antigenic drift (accumulation of mutations) or antigenic shift (swapping segment by reassortment).

Currently, one the most effective intervention for the control of seasonal or pandemic influenza disease is prophylactic vaccination. This practice requires that susceptible subjects receive annual doses of vaccine formulated with the most recent human viral isolates. Such vaccines are usually prepared from individual viruses, each one grown in embryonated chicken eggs or cultured cells and then blended in the final vaccine formulation in order to provide a broader coverage. Due to the rapid antigenic variation of the influenza virus, vaccines have to be periodically reformulated to incorporate emerging antigenic variants in order to maintain vaccine protective efficacy.

Vaccine effectiveness, therefore, depends upon the degree of antigenic similarity between the vaccine and virus strains circulating in humans. Furthermore, a certain proportion of vaccinated individuals, including the elderly, fail to develop protective immunity with the current vaccines.

A recent study performed with a phage-display antibody library has identified broadly neutralizing antibodies which are able to block infection across a broad spectrum of influenza virus subtypes (Jianhua Sui et. al. (2009) *Nat. Structural & Mol. Biol.* 16:265-273.) The ability of these antibodies to neutralize a broad spectrum of virus results from reacting with a sub-dominant and highly conserved epitope present in the stem region of the HA molecule, blocking infection by inhibiting membrane fusion rather than preventing receptor binding which is the predominant neutralizing mechanism induced by virus infection or vaccination. Design of a vaccine that displays these subdominant and highly conserved epitopes will elicit broadly neutralizing immune responses able to protect against a broad spectrum of influenza subtypes.

In order to produce the viral components needed to formulate the current vaccines, selected viruses are grown by infecting embryonated chicken eggs or cultured cells. This process depends upon the virus's ability to attach via the HA molecule to the sialic acid containing receptor on the cell surface, penetration, virus replication and isolation of viral progeny from the fluids in the egg or cultured cells. Truncation, re-engineering or remodeling of the viral HA would eliminate receptor binding and preclude virus replication and the production of such a vaccine.

Influenza VLPs are produced by the simultaneous expression of 2, 3 or 4 viral genes (M1, M2, HA and NA) with M1, M2, or (analogous matrix proteins) HA and NA being the main and essential components of the structure. See, e.g., U.S. Patent Publication Nos. 20080031895 and 20090022762. The DNA sequences encoding these genes are simultaneously or sequentially transfected into cells, where they are transcribed and translated into their respective proteins that self-assemble into virus-like particles. In contrast to viruses, modifications of the regions of the HA used for receptor binding and virus penetration do not interfere with the production, assembly or release of VLPs from the cells. That is, VLP production allows for the deletion and remodeling of major portions of HA bearing immunodominant and genetically variable regions of the molecule whereas the virus replication method does not allow for these modifications. Similar modification can also be introduced on the NA molecules, which is also displayed on the surface of the VLP vaccine.

However, there remains a need for influenza vaccine compositions and methods of making and using such compositions.

SUMMARY

Described herein are virus-like particles (VLPs) comprising at least one truncated and/or hybrid influenza antigenic protein (e.g., HA or NA). Also described are compositions comprising these VLPs, as well as methods for making and using these VLPs. The VLPs described herein are devoid of viral genetic material and therefore unable to replicate or cause infection; however given their morphological, biochemical and antigenic similarities to wild type virions, VLPs are highly immunogenic and able to elicit robust protective immune responses. Unlike virion inactivated based vaccines, VLPs are not infectious eliminating the need for chemical treatment, thus maintaining the native conformation. Furthermore, the present invention overcomes the issues associated with reformulating influenza vaccines each season, by providing broad protection against current and evolving influenza viruses.

Thus, in one aspect, disclosed herein is a virus-like particle (VLP) comprising provided herein is a virus-like particle (VLP) comprising at least one matrix protein (e.g., an influenza matrix protein such as M1, a thogoto matrix protein and an RSV matrix protein); and a modified influenza polypeptide (e.g., glycoprotein such as HA or NA), wherein the modification comprises a deletion of one or more amino acid residues outside the transmembrane and cytoplasmic tail domain of the influenza (e.g., HA) polypeptide. In certain embodiments, the deletion comprises a deletion at least 150 consecutive amino acid residues. In other embodiments, the deletion comprises more than one non-consecutive deletions. In still further embodiments, the influenza polypeptide (e.g., HA) comprises one or more amino acid mutations (substitutions and/or additions), for example, embodiments in which at least one proteolytic cleavage site and/or at least one linker is inserted into the modified influenza polypeptide (e.g., HA). The linker may be a known linker sequence or may be generated de novo for use in the molecules described herein. In any of the VLPs disclosed herein, the VLP can be polyvalent, namely can include a plurality of influenza antigenic proteins, including any combination of wild-type and/or modified influenza polypeptides as described herein. In addition in any of the VLPs described herein, the transmembrane and/or cytoplasmic domain of the modified influenza (e.g., HA or NA) polypeptide is replaced with a transmembrane and/or cytoplasmic domain from a different strain or subtype than the modified influenza polypeptide. Furthermore, any of the VLPs described herein may further comprise additional influenza proteins, for example one or more additional wild-type matrix proteins (M1 and/or M2), one or more additional modified (mutant and/or hybrid) matrix proteins (M1 and/or M2), one or more wild-type antigenic glycoproteins (HA and/or NA), one or more hybrid antigenic glycoproteins (HA and/or NA), one or more modified antigenic glycoproteins (HA and/or NA), one or more hybrid and modified antigenic polypeptides (HA and/or NA), one or more nucleoproteins (NPs), one or more PB1 proteins, one or more PB2 proteins, one or more PA proteins and combinations thereof. In certain embodiments, the VLP is polyvalent in that more than one antigenic glycoprotein (any combination of modified or wild-type) is expressed on the surface of the VLP (e.g., to generate immune responses). Any of the VLPs described herein can be expressed in a eukaryotic cell (e.g., a yeast cell, an insect cell, an amphibian cell, an avian cell, a plant cell or a mammalian cell) under conditions which permit the assembly and release of VLPs.

In another aspect, described herein is a host cell comprising any of the VLPs as described above. In certain embodiments, the host cell permits assembly and release of a VLP as described herein from one or more vectors encoding the polypeptides of the VLP. In certain embodiments, the eukaryotic cell is selected from the group consisting of a yeast cell, an insect cell, an amphibian cell, an avian cell, a plant cell or a mammalian cell.

In yet another aspect, provided herein is a method of producing any of the VLPs described herein, the method comprising the steps of transfecting one or more vectors encoding at least one matrix protein and at least one modified influenza (e.g., HA) polypeptide into a suitable host cell and expressing the combination of protein under conditions that allow VLP formation. In any of the VLPs, the matrix protein can be an influenza M1 protein, a thogoto matrix protein and an RSV matrix protein. In other embodiments, additional or the same vectors may encode additional proteins, for example additional influenza proteins (e.g., NA proteins, etc.). In certain embodiments, the at least one vector further comprises a sequence encoding an influenza M2 protein. The expression vector may be a plasmid, a viral vector, a baculovirus vector or a non-viral vector. The vectors may encode one, more than one or all of the proteins of the VLP. In any of the methods of VLP production described herein, one or more of the vectors can be stably transfected into the host cell. In certain embodiments, the at least one matrix protein and the modified influenza HA polypeptide are encoded on separate vectors and the vector encoding the at least one matrix protein is stably transfected into the cell prior to transfection with the vector encoding the modified influenza HA polypeptide protein. The proteins encoded by the vectors may be full-length wild-type, full-length mutants, truncated wild-type, truncated mutants, and/or hybrid proteins include full-length and/or truncated wild-type or mutant proteins. The cell can be a eukaryotic cell, for example, a yeast cell, an insect cell, an amphibian cell, an avian cell, a plant cell or a mammalian cell. In certain embodiments, at least one M protein comprises an influenza matrix protein.

In a still further aspect, described herein is an immunogenic composition comprising at least one VLP as described herein. In certain embodiments, the immunogenic composition further comprises an adjuvant. Any of the immunogenic compositions described herein may include at least two VLPs comprising different modified influenza (e.g., HA) polypeptides. In certain embodiments, the composition comprises and contains at least two VLPs, each VLP comprising a different modified HA protein or a single VLP displaying two or more remodeled HA or NA glycoproteins on its surface (e.g., polyvalent VLP). In still further embodiments, the immunogenic composition further comprises an adjuvant.

In a still further aspect, provided herein is a method of generating an immune response to influenza in a subject, the method comprising administering to the subject (e.g., human) an effective amount of a VLP and/or immunogenic composition as described herein to the subject. In certain embodiments, the composition is administered mucosally, intradermally, subcutaneously, intramuscularly, or orally. In certain embodiments, the methods generate an immune response to multiple strains or subtypes of influenza, thereby providing a "universal" vaccine that protects the subject against influenza infection from various influenza viruses and/or over time (more than one flu season).

Any of the methods may involve multiple administrations (e.g., a multiple dose schedule).

In another aspect, a packaging cell line is provided for producing influenza VLPs as described herein. The cell line is stably transfected with one or more polynucleotides encoding at least two M proteins and upon introduction and expression of the one or more influenza protein-encoding sequences not stably transfected into the cell, the VLP is produced by the cell. In certain embodiments, sequences encoding M1 and/or M2 are stably integrated into the packaging cell line and sequences encoding the modified HA proteins expressed on the surface of the VLP are introduced into the cell such that the VLP is formed. In other embodiments, sequences encoding one or more of the modified HA proteins are stably integrated into the cell to form a packaging cell line and VLPs are formed upon introduction of sequences encoding the at least two M proteins. The packaging cell may be an insect, plant, mammalian, bacterial or fungal cell. In certain embodiments, the packaging cell is a mammalian (e.g., human) cell line.

Figure 1:
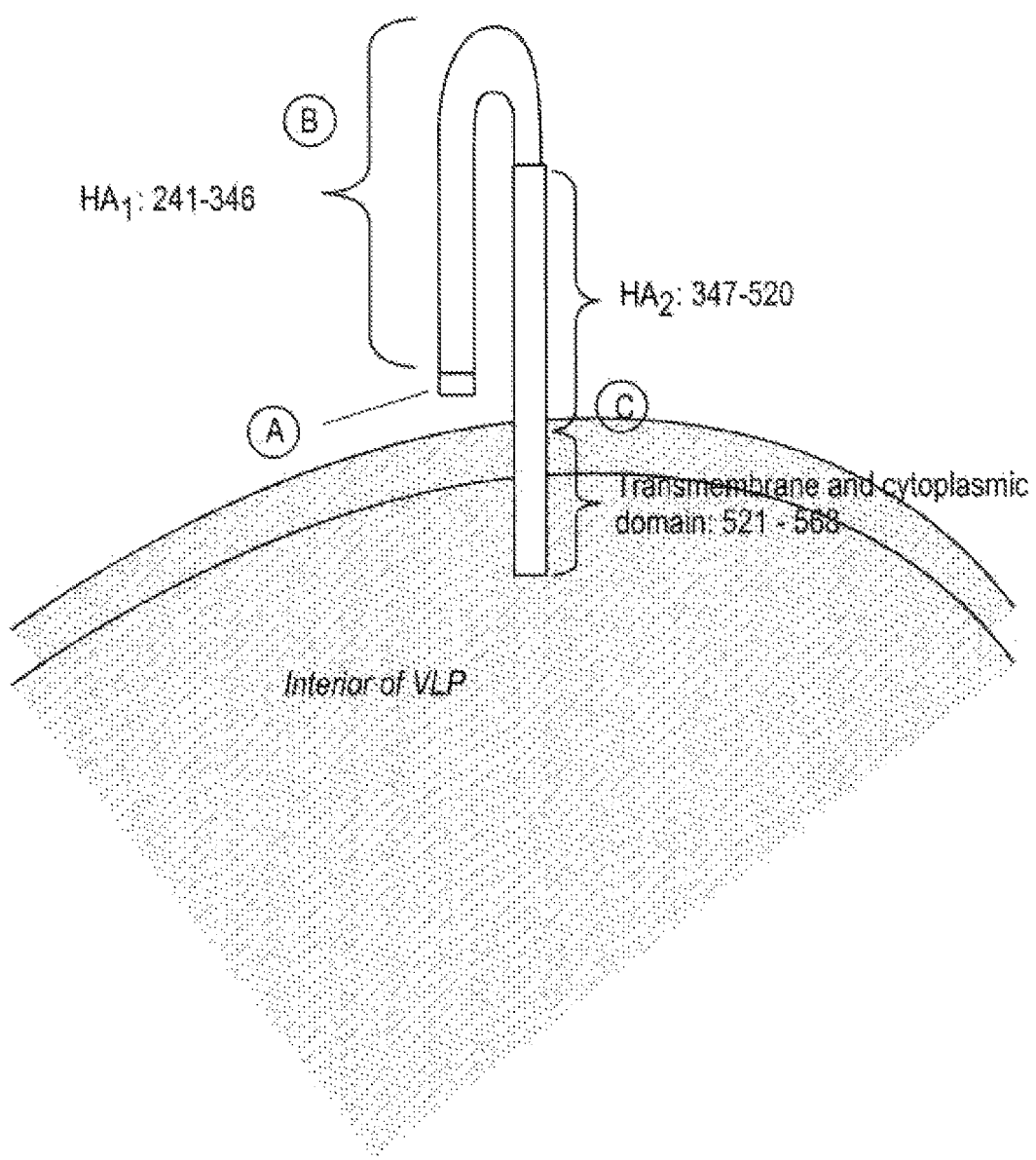
FIG. 1 depicts a schematic of the structure of a remodeled HA molecule where a portion of the HA1 sequence is removed, an insertion is introduced between the signal peptide and the remaining portion of the HA1 molecule. Mutations are introduced to prevent disulfide bond formation as specified in the schematic and sequence. The HA2 portion of the molecule is maintained in its entirety, including the transmembrane and cytoplasmic domains. This construct is identified as "1TA" (SEQ ID NOs:1 and 2). "A" represents the $NH_2$ terminal sequence of the HA1 molecule, "B" represents the remaining portion of the HA1 molecule, and "C" represents the HA2 portion of the remodeled HA molecule.

FIG. 2 shows and schematic of a second remodeled HA molecule where the NH2 terminal sequence after removal of the signal peptide includes a sequence forming part of the conserved epitope and a C20 residue for the formation of an inter-chain disulfide bond. This genetically linked to a truncated portion of HA1 (R241-L333) and the entire HA2 fragment. This construct is identified as "2TA" (SEQ ID NOs:3 and 4). "A" represents the $NH_2$ terminal sequence of the HA1 molecule, "B" represents the remaining portion of the HA1 molecule, and "C" represents the HA2 portion of the remodeled HA molecule.

FIG. 3 depicts a schematic structure of a remodeled HA where the NH2 terminal portion (D17-P65) after removal of the signal peptide is connected to a truncated region of the HA1 (M281-R346) through a designed 12 amino acid linker (DIGPGKVGYGPG, SEQ ID NO:11); this whole fragment is linked to a complete HA2 (G347-I568) to which mutations V412 to D412 and L419 to G419 has been introduced to prevent protein aggregation. This construct is identified as "3TA" (SEQ ID NOs:5 and 6). "A" represents the $NH_2$ terminal sequence of the HA1 molecule, "B" represents the designed 12 amino acid linker, and "C" represents the truncated region of the HA1 molecule linked to the complete HA2 portion of the remodeled HA molecule.

FIG. 4 shows a schematic of a truncated HA molecule encompassing the entire amino acids sequence, after removal of the signal peptide, of the HA2 fragment (G347-I568 including the extracellular, transmembrane and cytoplasmic domains. This construct is identified as "4TA" (SEQ ID NOs:7 and 8). "A" represents the extracellular domain of the HA2 fragment.

FIGS. 5A and 5B, are schematics of a re-engineered HA molecule in which two proteolytic cleavage sites (10 amino acid insertions each, PQRERRRKKR, SEQ ID NO:12) has been introduced within the sequence of the HAL one between positions P65 and L66 and the other between positions 1280 and M281. Following expression and folding of the modified HA into its native conformation, the globular head of the structure, which displays the most dominant and highly variable antigenic sites, can be removed by proteases treatment exposing the subdominant and highly conserved epitopes that elicit broadly protective immune responses (See FIG. 5B). The structure is maintained by an inter-chain disulfide bond between C20 and C483. This construct is identified as "5TA" (SEQ ID NOs:9 and 10). For FIG. 5A, "A" represents a third fragment of the HA1 molecule separated from the second fragment of the HA1 molecule and the first fragment ($NH_2$ terminal fragment) of the HA1 molecule, "B" represents the proteolytic cleavage sites of the HA molecule, "C" represents the second fragment of the HA1 molecule, and "D" represents the HA2 fragment, including the extracellular domain, and the transmembrane and cytoplasmic domains.

FIGS. 6A and 6B are schematic of exemplary DNA vectors carrying the influenza genes within determined positions and under indicated regulatory elements for the production of VLPs in mammalian cells or baculovirus-insect cell expression system.

FIGS. 7A and 7B depict examples of strategies employed for the transfection of vectors into mammalian cells, expression of proteins and selection of stably transfected cell lines for the continuous production of VLPs.

FIG. 8A through 8C show results of fluorescent activated cell sorting (FACS) of M1/M2 stably transfected mammalian cells using an anti-M2 antibody as primary and a fluorescein FITC labeled anti-mouse as secondary antibody. FIG. 8A shows unstained control. FIG. 8B shows isotype control and FIG. 8C staining for surface expression of M2.

FIGS. 9A and 9B depict Western blots of cell lysates of M1/M2 stably transfected mammalian cells. FIG. 9A shows protein levels in MDCK cells (lane 1 shows results from normal MDCK cells and lane 2 shows results from MDCK cells constitutively expressing M1/M2 proteins. FIG. 9B shows results from CHO cells: lane 1 shows a negative control (CHO cell lysate); lane 2 shows CHO cells infected with influenza virus PR8; lane 3 shows CHO cells constitutively expressing M1/M2 (clone 1); and lane 4 shows CHO cells constitutively expressing M1/M2 (clone 2.)

FIG. 10 shows a western blot of cell lysates of M1/M2 and NA/HA (remodeled) transfect mammalian cell. FIG. 10 shows protein levels in CHO cell lysates and concentrated/purified culture supernatant; lane 1 influenza virus control (HA5/NA1 reassorted PR8), lane 2 untransfected CHO cells as negative control, lanes 3 and 5 cell lyzates of CHO transfected with M1/M2 together with NA/HA remodeled 5TA (lane 3) and NA/HA remodeled 3TA (lane 5). Lanes 4 and 6 show the concentrated/purified culture supernatant of CHO cells transfected with M1/M2 together with NA/remodeled HAs-5TA and 3TA respectively.

FIG. 11 shows electron micrograph images of VLPs produced in CHO cells and purified from the culture supernatant of M1/M2-NA/HA transfected cells.

DETAILED DESCRIPTION

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag); Fundamental Virology, Second Edition (Fields & Knipe eds., 1991, Raven Press, New York).

All publications, patents and patent applications cited herein are hereby incorporated by reference in their entirety.

As used in this specification and the appended claims, the singular forms "a," "an" and "the" include plural references unless the content clearly dictates otherwise. Thus, for example, reference to "a VLP" includes a mixture of two or more such VLPs.

DEFINITIONS

As used herein, the terms "sub-viral particle" "virus-like particle" or "VLP" refer to a nonreplicating, viral shell. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding (e.g., Examples). Alternatively, cryoelectron microscopy can be performed on vitrified aqueous samples of the VLP preparation in question, and images recorded under appropriate exposure conditions. Additional methods of VLP purification include but are not limited to chromatographic techniques such as affinity, ion exchange, size exclusion, and reverse phase procedures.

A used herein, the term "hybrid" or "chimeric" refers to a molecule (e.g., protein or VLP) that contains portions thereof, from at least two different proteins. For example, a hybrid influenza HA protein refers to a protein comprising at least a portion of an influenza HA protein (for example a portion containing one or more antigenic determinants) and portions of a heterologous protein (e.g., the cytoplasmic and/or transmembrane domain of a different influenza protein or a different viral protein, for example an RSV or VSV protein). It will be apparent that a hybrid molecule as described herein can include full-length proteins fused to additional heterologous polypeptides (full length or portions thereof) as well as portions proteins fused to additional heterologous polypeptides (full length or portions thereof). It will also be apparent that the hybrids can include wild-type sequences or mutant sequences in any one, some or all of the heterologous domains.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, and/or sequence elements controlling an open chromatin structure see e.g., McCaughan et al. (1995) PNAS USA 92:5431-5435; Kochetov et al (1998) FEBS Letts. 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when active. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of one or more sequences of interest in a host cell. Thus, the term includes cloning and expression vehicles, as well as viral vectors. The term is used interchangeable with the terms "nucleic acid expression vector" and "expression cassette."

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any unacceptable biological effects or interacting in a deleterious manner with any of the components of the composition in which it is contained.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

As used herein the term "adjuvant" refers to a compound that, when used in combination with a specific immunogen (e.g. a VLP) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

As used herein an "effective dose" generally refers to that amount of VLPs of the invention sufficient to induce immunity, to prevent and/or ameliorate an infection or to reduce at least one symptom of an infection and/or to enhance the efficacy of another dose of a VLP. An effective dose may refer to the amount of VLPs sufficient to delay or minimize the onset of an infection. An effective dose may also refer to the amount of VLPs that provides a therapeutic benefit in the treatment or management of an infection. Further, an effective dose is the amount with respect to VLPs of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

As used herein, the term "effective amount" refers to an amount of VLPs necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to VLPs of the invention. The term is also synonymous with "sufficient amount."

As used herein, the term "multivalent" refers to VLPs which have multiple antigenic proteins against multiple types or strains of infectious agents.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons, interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As used herein the term "protective immune response" or "protective response" refers to an immune response mediated by antibodies against an infectious agent, which is exhibited by a vertebrate (e.g., a human), that prevents or ameliorates an infection or reduces at least one symptom thereof. VLPs of the invention can stimulate the production of antibodies that, for example, neutralize infectious agents, blocks infectious agents from entering cells, blocks replication of said infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates influenza infection or reduces at least one symptom thereof.

As use herein, the term "antigenic formulation" or "antigenic composition" refers to a preparation which, when administered to a vertebrate, e.g. a mammal, will induce an immune response.

As used herein, the term "vaccine" refers to a formulation which contains VLPs of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

General Overview

Described herein are influenza VLPs that can be used to protect and/or treat humans from influenza infection. In particular, described herein is a VLP influenza vaccine that induces a strong immunological protective response against a variety of distinct flu viruses by deletion of amino acid residues and peptide sequences which create or compose a part of the immunodominant and/or highly variable regions of the virus (e.g., antigenic portions). This allows for otherwise immunologically cryptic epitopes becoming dominant and highly immunogenic.

To generate a structurally modified HA molecule, the DNA sequence coding for this glycoprotein is rearranged by truncations, insertions, mutations or combinations thereof creating an open reading frame (ORF) for the synthesis of a remodeled HA molecule. As noted above, the VLPs described herein elicit a distinct immune response as compared to the response stimulated by the viral infection or immunization with different vaccine compositions or formulations, including previously described VLPs. The broadly neutralizing response elicited by this VPL vaccine will provide heterosubtypic protection against multiple influenza virus strains or subtypes.

Virus-Like Particles

When sequences encoding influenza proteins are expressed in eukaryotic, the proteins have been shown to self-assemble into noninfectious virus-like particles (VLP). See, Latham & Galarza (2001) *J. Virol.* 75(13):6154-6165; Galarza et al. (2005) *Viral. Immunol.* 18(1):244-51; and U.S. Patent Publications 2008/0233150; 2008/0031895 and 2009/0022762.

The present disclosure relates to influenza VLPs from the plasma membrane of eukaryotic cells, which VLPs carry on their surfaces modified antigenic influenza proteins. This VLP, alone or in combination with one or more additional VLPs and/or adjuvants, stimulates an immune response that protects against influenza infection.

The VLPs described herein (also called sub-viral structure vaccine (SVSV)) is typically composed of viral proteins produced from naturally occurring and/or mutated nucleic acid sequences of genes coding for matrix protein M (also known as M1) and, optionally, M2 protein. The matrix protein M is a universal component for the formation of all possible polyvalent sub-viral structure vaccine combinations. The M1 and M2 proteins may be derived from any virus. In certain embodiments, the M1 and/or M2 protein of the VLP is derived from an influenza matrix protein. In other embodiments, the M1 and/or M2 protein of the VLP is derived from RSV or thogoto-virus. The M1 and/or M2 proteins may be modified (mutated), for example as disclosed herein or in U.S. Patent Publications 2008/0031895 and 2009/0022762.

Influenza proteins derived from the same or different families of enveloped viruses can be selected for incorporation onto the surface of the vaccine. The incorporation of influenza proteins into the same vaccine particle can be facilitated by replacing the cytoplasmic tail and transmembrane amino acid sequences with those from a common glycoprotein via alterations in the nucleic acids coding for these proteins. This approach allows for the design of a large number of possible polyvalent sub-viral vaccine combinations.

1. Modified Influenza Antigenic Polypeptides

As noted above, the VLPs described herein comprise modified (e.g., truncated, deletions, hybrid, etc.) influenza antigenic polypeptides.

In certain embodiments, the modified influenza antigen is a hemagglutinin (HA) polypeptide. The major functions of the hemagglutinin (HA) molecule are receptor-binding and membrane fusion activity, critical steps in the initiation of viral infection. In addition, HA is the major surface antigen of the virus against which neutralizing antibodies are produced. The precursor molecule (HA0) is cleaved into two polypeptides (HA1) and (HA2) and covalently linked by a single disulphide bond. Cleavage of the HA0 activates the fusion peptide on the NH2 terminal of the HA2 subunit and activates the fusion potential of the HA, an essential process required for virus infectivity.

The most important and immunological dominant antigenic sites on the HA structure reside on the head of the molecule, primarily formed by the HA1 subunit. Changes in these antigenic regions by mutations (antigenic drift) or HA swapping (antigenic shift) allows for the virus to escape host neutralizing antibodies and initiate infection of new cells. In addition to these sites, subdominant and highly conserved epitopes are present on the stem portion of the structure; however, because of immunological hierarchy these sites are mainly unrecognized by the immune system and unable to generate a significant antibody response. Nonetheless, antibodies targeting these regions are able to block infection by inhibiting membrane fusion and therefore virus entry.

Thus, the vaccine described in this invention is based on expressing, in a VLP, truncated, re-engineered and remodeled HA molecules that lack the major immunodominant epitopes and predominantly display subdominant antigenic sites present on the stem portion of the molecule. These structurally modified HAs are incorporated on the surface of virus-like particles (VLP) forming single non-infectious protective particle (SNIPP) influenza vaccines.

In certain aspects, the modified (remodeled) HA polypeptides lack a portion of the HA1 domain, for example by deleting some or all of the immunodominant epitopes, while maintaining a small NH2 terminal region containing the translocation signal sequence which is linked to alternative configurations of HA1 and HA2 subunits. The deletions (truncations) can be of any length, for example from 10 to 300 base pairs (or any value therebetween, for example, 10, 15, 20, 25, 50, 75, 100, 125, 150, 175, 200, 225, 250, 275, 300 or more base pairs). In addition, the deletions can be of consecutive base pairs or, alternatively, base pairs can be deleted in different regions of the HA polypeptide, for example deleting 10 or more base pairs at the N-terminal and additional base pairs (10 to 300 or even more) in the central region of the molecule (e.g., a region of 10 or more base pairs C-terminal to the translocation signal sequence). Additional modifications include, but are not limited to, addition of linkers, mutation of one or more residues of the polypeptide and the like. The specific modifications of the HA molecule can be readily performed at the DNA level and subsequently sub-clone together with the combination of genes required for VLP assembly.

Thus, the antigenic influenza proteins (e.g., HA) provided in the VLP can be modified in any way, for example via deletions of one or more amino acids and/or mutations of one amino acid.

In one embodiments, an influenza HA polypeptide is modified by deleting amino acids near the N-terminal of the HA polypeptide. For example, as numbered relative to wild-type HA sequence UniProt KB Q6DQ33, the residues from H24 to G240 may be deleted. Optionally, other portions of the HA1 NH2 terminal are deleted while retaining amino acids D17 to Y23 and the secretion signal sequence. The retained small sequence maintains residue C20 which promotes the formation of an inter-chain disulfide bond with C483 and stabilizes the molecule. The remaining region of HA1 (R241-L333) forms a series of beta sheets interspersed with bend conserving residue C294 which forms a disulfide bond with C318. Optionally, a residue at position C290 is mutated to G to prevent potential disulfide bond formation with either C294 or C318.

In other embodiments, a modified (remodeled) HA comprises the NH2 terminal of HA1 (e.g., D17 to P65, as numbered relative to wild-type HA sequence UniProt KB Q6DQ33) which includes residues that promote disulfide bonding (e.g. C20 and C483, as numbered relative to wild-type HA sequence UniProt KB Q6DQ33). Such modified HA polypeptides can be linked to additional regions of HAL for examples residues 241 to 346, as numbered relative to wild-type HA sequence UniProt KB Q6DQ33, which includes the enzymatic cleavage site and unchanged C290 to promote the formation of a disulfide bond with C58.

In yet other embodiments, a modified HA that includes the NH2 terminal portion of the HA1 (D17 to P65, as numbered relative to wild-type HA sequence (SEQ ID NO:13) such as UniProt KB Q6DQ33) is provided. Optionally, after the cleavage of the signal peptide, this fragment can be linked to another portion of the HA1 (e.g., M281-R346, as numbered relative to wild-type HA sequence UniProt KB Q6DQ33), for example through a peptide linker. Any peptide linker of any length can be used. In certain embodiments, the peptide linker is between 5 and 25 amino acids (including any number therebetween), for example a 12 amino acid linker (DIGPGKVGYGPG, SEQ ID NO:11). In this construct, the residues that promote the formation of disulfide bonds are maintained (e.g., C20-C483, C294-C318 and C58-C290 pairing residues, as numbered relative to wild-type HA sequence UniProt KB Q6DQ33).

Any of the modified HA1 polypeptides (fragments) described herein can be operably linked to an HA2 fragment (e.g., an HA2 fragment comprising residues G3474568, as numbered relative to wild-type HA sequence UniProt KB Q6DQ33)) comprising the transmembrane domain and cytoplasmic tail. See, Example 1 and Figures. In addition, mutations may be introduced into one or more amino acids of the HA2 polypeptide, for example, mutations of residues that inhibit or prevent protein aggregation (e.g., V412 to D412 and L419 to G419, as numbered relative to wild-type HA sequence UniProt KB Q6DQ33). See, e.g., FIG. 3.

In still further embodiments, a modified HA comprises of an entire HA2 fragment linked to the secretion signal peptide. This construct comprises a secretion signal sequence, the HA2 extracellular (e.g., 347-520, as numbered relative to wild-type HA sequence UniProt KB Q6DQ33) transmembrane and cytoplasmic (e.g., 521-568, as numbered relative to wild-type HA sequence UniProt KB Q6DQ33) domains. The signal peptide is removed during transcription/translocation and it is not present in the HA2 structure incorporated onto the VLP vaccine; as it is the case for the other remodeled HAs. It will be apparent that the transmembrane domain and cytoplasmic tail at the carboxyl terminal of the HA2 subunits can be replaced with analogous sequences of an influenza virus from which the M1 protein is derived or the sequence that best interacts with an M1 analogue. See, e.g., FIG. 4.

In another embodiment, the HA is modified by inserting two or more 12-mers multi basic proteolytic cleavage sites within the sequence of the protein. Non-limiting examples of suitable insertion sites, as numbered relative to wild-type HA sequence UniProt KB Q6DQ33, include between P65 and L66 and/or between 1280 and M281. In addition, one or more residues of the native proteolytic cleavage site (KKR to GGG) can also be mutated in order to prevent cleavage at this location. Proteases treatment of this molecule removes the globular head of the HA exposing the conserved epitopes formed by the HA2 stem and remaining portions of HAL See, e.g., FIGS. 5A and B.

2. Polypeptide-Encoding Sequences

The VLPs produced as described herein are conveniently prepared using standard recombinant techniques. Polynucleotides encoding the VLP-forming protein(s) are introduced into a host cell and, when the proteins are expressed in the cell, they assembly into VLPs.

Polynucleotide sequences coding for molecules (structural and/or antigen polypeptides, including modified antigenic (e.g., HA) polypeptides) that form and/or are incorporated into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

The VLPs described herein are typically formed by expressing sequences encoding M1 and at least one modified influenza (e.g., HA antigen) in a cell, optionally with an M2 protein. The expressed proteins self-assemble into VLPs with the antigenic glycoproteins decorating the surface of the VLP.

In certain embodiments, the matrix-encoding sequences are RSV matrix proteins. In other embodiments, the matrix-encoding sequences are influenza matrix proteins. It will also be apparent that the matrix-encoding sequences can contain one or more mutations (modifications), for example the modified matrix proteins as described in U.S. Patent Publications 2008/0031895 and 2009/0022762. The VLPs described herein may further comprise additional influenza proteins (wild-type, modified (mutants) and/or hybrids of wild-type or mutants).

Any of the proteins used in the VLPs described herein may be hybrid (or chimeric) proteins. It will be apparent that all or parts of the polypeptides may be replaced with sequences from other viruses and/or sequences from other influenza strains. In one exemplary embodiment, any of the proteins of the VLP may be hybrids in that they include heterologous sequences encoding the transmembrane and/or cytoplasmic tail domains, for example domains from influenza proteins such as HA or NA. See, e.g., U.S. Patent Publication Nos. 2008/0031895 and 2009/0022762.

Preferably, the sequences employed to form influenza VLPs exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring influenza polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring polynucleotide sequence.

Any of the sequences described herein may further include additional sequences. For example, to further to enhance vaccine potency, hybrid molecules are expressed and incorporated into the sub-viral structure. These hybrid molecules are generated by linking, at the DNA level, the sequences coding for the matrix protein genes with sequences coding for an adjuvant or immuno-regulatory moiety. During sub-viral structure formation, these hybrid proteins are incorporated into or onto the particle depending on whether M1 or optional M2 carries the adjuvant molecule. The incorporation of one or more polypeptide immunomodulatory polypeptides (e.g., adjuvants describe in detail below) into the sequences described herein into the VLP may enhance potency and therefore reduces the amount of antigen required for stimulating a protective immune response. Alternatively, as described below, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors.

3. Expression Vectors

Once the constructs comprising the sequences encoding the polypeptide(s) desired to be incorporated into the VLP have been synthesized, they can be cloned into any suitable vector or replicon for expression. Numerous cloning vectors are known to those of skill in the art, and one having ordinary skill in the art can readily select appropriate vectors and control elements for any given host cell type in view of the teachings of the present specification and information known in the art about expression. See, generally, Ausubel et al, supra or Sambrook et al, supra.

Non-limiting examples of vectors that can be used to express sequences that assembly into VLPs as described herein include viral-based vectors (e.g., retrovirus, adenovirus, adeno-associated virus, lentivirus), baculovirus vectors (see, Examples), plasmid vectors, non-viral vectors, mammalians vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9): 815-821, 1994; Kozak, M., J Cell Biol 108(2):229-241, 1989; Kozak, M., and Shatkin, A. J., Methods Enzymol 60:360-375, 1979).

For example, typical promoters for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs as described herein (Chapman et al., Nuc. Acids Res. (1991) 19:3979-3986).

Enhancer elements may also be used herein to increase expression levels of the mammalian constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

It will be apparent that one or more vectors may contain one or more sequences encoding proteins to be incorporated into the VLP. For example, a single vector may carry sequences encoding all the proteins found in the VLP. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector. Furthermore, vectors may contain additional gene expression controlling sequences including chromatin opening elements which prevent transgene silencing and confer consistent, stable and high level of gene expression, irrespective of the chromosomal integration site. These are DNA sequence motifs located in proximity of house-keeping genes, which in the vectors create a transcriptionally active open chromatin environment around the integrated transgene, maximizing transcription and protein expression, irrespective of the position of the transgene in the chromosome.

In addition, one or more sequences encoding non-influenza proteins may be expressed and incorporated into the VLP, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

4. VLP Production

As noted above, influenza proteins expressed in a eukaryotic host cell have been shown to self-assemble into non-infectious virus-like particles (VLP). Accordingly, the sequences and/or vectors described herein are then used to transform an appropriate host cell. The construct(s) encoding the proteins that form the VLPs described herein provide efficient means for the production of influenza VLPs using a variety of different cell types, including, but not limited to, insect, fungal (yeast) and mammalian cells.

Preferably, the sub-viral structure vaccines are produced in eukaryotic cells following transfection, establishment of continuous cell lines (using standard protocols) and/or infection with DNA constructs that carry the influenza genes of interest as known to one skilled in the art. The level of expression of the proteins required for sub-viral structure formation is maximized by sequence optimization of the eukaryotic or viral promoters that drive transcription of the selected genes. The sub-viral structure vaccine is released into the culture media, from where it is purified and subsequently formulated as a vaccine. The sub-viral structures are not infectious and therefore inactivation of the VLP is not required as it is for some killed viral vaccines The ability of influenza polypeptides expressed from sequences as described herein to self-assemble into VLPs with antigenic glycoproteins presented on the surface allows these VLPs to be produced in many host cell by co-introduction of the desired sequences. The sequence(s) (e.g., in one or more expression vectors) may be stably and/or transiently integrated in various combinations into a host cell.

Suitable host cells include, but are not limited to, bacterial, mammalian, baculovirus/insect, yeast, plant and *Xenopus* cells. For example, a number of mammalian cell lines are known in the art and include primary cells as well as immortalized cell lines available from the American Type Culture Collection (A.T.C.C.), such as, but not limited to, MDCK, BHK, VERO, MRC-5, WI-38, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

Similarly, bacterial hosts such as *E. coli, Bacillus subtilis*, and *Streptococcus* spp., will find use with the present expression constructs. Yeast hosts useful in the present disclosure include inter alia, *Saccharomyces cerevisiae, Candida albicans, Candida maltosa, Hansenula polymorpha, Kluyverornyces fragilis, Kluyveromyces lactis, Pichia guillerimondii, Pichia pastoris, Schizosaccharomyces pombe* and *Yarrowia lipolytica*. Fungal hosts include, for example, *Aspergillus*.

Insect cells for use with baculovirus expression vectors include, inter alia, *Aedes aegypti, Autographa californica, Bombyx mori, Drosophila melanogaster, Spodoptera frugiperda*, and *Trichoplusia ni*. See, Latham & Galarza (2001) *J. Virol.* 75(13):6154-6165; Galarza et al. (2005) *Viral. Immunol.* 18(1):244-51; and U.S. Patent Publications 200550186621 and 20060263804.

Cell lines expressing one or more of the sequences described above can readily be generated given the disclosure provided herein by stably integrating one or more expression vector constructs encoding the proteins of the VLP. The promoter regulating expression of the stably integrated influenza sequences (s) may be constitutive or inducible. Thus, a cell line can be generated in which one or more both of the matrix proteins are stably integrated such that, upon introduction of the sequences described herein (e.g., hybrid proteins) into a host cell and expression of the proteins encoded by the polynucleotides, non-replicating viral particles that present antigenic glycoproteins are formed.

In certain embodiments, a mammalian cell line that stably expressed two or more antigenically distinct influenza proteins is generated. Sequences encoding M1, M2 and/or additional glycoproteins (e.g., from the same or different virus strains) can be introduced into such a cell line to produce VLPs as described herein. Alternatively, a cell line that stably produces an M1 protein (and, optionally, M2) can be generated and sequences encoding the antigenic influenza protein(s) from the selected strain(s) introduced into the cell line, resulting in production of VLPs presenting the desired antigenic glycoproteins.

The parent cell line from which an VLP-producer cell line is derived can be selected from any cell described above, including for example, mammalian, insect, yeast, bacterial cell lines. In a preferred embodiment, the cell line is a mammalian cell line (e.g., 293, RD, COS-7, CHO, BHK, MDCK, MDBK, MRC-5, VERO, HT1080, and myeloma cells). Production of influenza VLPs using mammalian cells provides (i) VLP formation; (ii) correct post translation modifications (glycosylation, palmitylation) and budding; (iii) absence of non-mammalian cell contaminants and (iv) ease of purification.

In addition to creating cell lines, influenza-encoding sequences may also be transiently expressed in host cells. Suitable recombinant expression host cell systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.)), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media PA; Clontech), expression in yeast (Rosenberg, S. and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology:

Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997).

When expression vectors containing the altered genes that code for the proteins required for sub-viral structure vaccine formation are introduced into host cell(s) and subsequently expressed at the necessary level, the sub-viral structure vaccine assembles and is then released from the cell surface into the culture media (FIG. 7).

Depending on the expression system and host selected, the VLPs are produced by growing host cells transformed by an expression vector under conditions whereby the particle-forming polypeptide(s) is(are) expressed and VLPs can be formed. The selection of the appropriate growth conditions is within the skill of the art. If the VLPs are formed and retained intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. J. Virol. (1993) 67:6929-6936), as well as standard purification techniques including, e.g., ion exchange and gel filtration chromatography.

Compositions

VLPs produced as described herein can be used to elicit an immune response when administered to a subject. As discussed above, the VLPs can comprise a variety of antigens (e.g., one or more modified influenza antigens from one or more strains or isolates). Purified VLPs can be administered to a vertebrate subject, usually in the form of vaccine compositions. Combination vaccines may also be used, where such vaccines contain, for example, other subunit proteins derived from influenza or other organisms and/or gene delivery vaccines encoding such antigens.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 10 (or more) mg, more preferably about 1 µg to about 300 µg, of VLP/antigen.

Sub-viral structure vaccines are purified from the cell culture media and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

A carrier is optionally present in the compositions described herein. Typically, a carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Such carriers are well known to those of ordinary skill in the art.

Additionally, these carriers may function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immuno stimulating agents such as muramyl peptides (see below) or bacterial cell wall components), such as for example (a) MF59 (International Publication No. WO 90/14837), containing 5% Squalene, 0.5% TWEEN 80 (polysorbate 80; polyoxyethylene sorbitan monooleate), and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80 (polysorbate 80; polyoxyethylene sorbitan monooleate), 5% pluronic-blocked polymer L121, and thr-MDP (see below) either microfluidized into a submicron emulsion or vortexed to generate a larger particle size emulsion, and (c) RIBI™ adjuvant system (RAS) (oil-in-water emulsion), (Ribi Immunochem, Hamilton, Mont.) containing 2% Squalene, 0.2% TWEEN 80 (polysorbate 80; polyoxyethylene sorbitan monooleate), and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as STIMULON™. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) J. Immunology 144:290-298, Weber et al. (1987) J. Exp. Med. 166: 1716-1733, Gansbacher et al. (1990) J. Exp. Med. 172:1217-1224, and U.S. Pat. No. 4,738,927-); IL-3 and IL-4 (Tepper et al. (1989) Cell 57:503-512, Golumbek et al. (1991) Science 254:713-716, and U.S. Pat. No. 5,017,691); IL-5 and IL-6 (Brakenhof et al. (1987) J. Immunol. 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) Methods in Enz. 78:387-394, Twu et al. (1989) *Proc. Natl. Acad. Sci. USA* 86:2046-2050, and Faktor et al. (1990) *Oncogene* 5:867-872); β-interferon (Seif et al. (1991) *J. Virol.* 65:664-671); γ-interferons (Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942-951); CD3 (Krissanen et al. (1987) Immunogenetics 26:258-266); ICAM-1 (Altman et al. (1989) *Nature* 338:512-514, Simmons et al. (1988) *Nature* 331:624-627); ICAM-2, LFA-1, LFA-3 (Wallner et al. (1987) *J. Exp. Med.* 166:923-932); MHC class I molecules, MHC class II molecules, B7.1-β2-microglobulin (Parnes et al. (1981) *Proc. Natl. Acad. Sci. USA* 78:2253-2257); chaperones such as calnexin; and MHC-linked transporter proteins or analogs thereof (Powis et al. (1991) *Nature* 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids encoding one or more of the above-identified polypeptides can be digested with appropriate restriction enzymes, and DNA fragments containing the particular gene of interest can be inserted into a gene transfer vector (e.g., expression vector as described above) using standard molecular biology techniques. (See, e.g., Sambrook et al., supra, or Ausubel et al. (eds) Current Protocols in Molecular Biology, Greene Publishing and Wiley-Interscience).

Administration

The VLPs and compositions comprising these VLPs can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration. Multiple doses can be administered by the same or different routes. In a preferred embodiment, the doses are intranasally administered.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting. Thus, it will be apparent that while the modifications disclosed are numbered with respect to a given wild-type HA sequence (e.g., UniProt KB Q6DQ33), corresponding mutations can be readily made in other HA sequences.

Examples

Example 1: Generation of Truncated, Re-Engineered and Remodeled HA Molecules

Various modified HA molecules were designed as follows.

A remodeled HA molecule was generated by deleting a portion (217aa, from H23 to G240) of the HA1 fragment, maintaining amino acids D17 to Y23 at the NH2 terminal after removal of the secretion signal sequence. This small sequence maintained residue C20 which promotes the formation of an inter-chain disulfide bond with C483 and stabilizes the molecule. The remaining region of HA1 R241-L333 forms a series of beta sheets interspersed with bend conserving residue C294 which forms a disulfide bond with C318. Furthermore, a residue at position C290 was mutated to G to prevent potential disulfide bond formation with either C294 or C318. This HA1 fragment was genetically linked to the entire HA2 fragment comprising the transmembrane domain and cytoplasmic tail.

The resulting construct is designated "1TA remodeled HA" and is depicted in FIG. 1. DNA and amino acid sequences of this construct are as follows:

```
Nucleotide Sequence of Remodeled HA 1TA (SEQ ID
NO: 1):
ATGGAGAAAATAGTGCTTCTTTTTGCAATAGTCAGTCTTGTTAAAAGTGA

TCAGATTTGCATTGGTTACAGGATGGAGTTCTTCTGGACAATTTTAAAGC

CGAATGATGCAATCAACTTCGAGAGTAATGGAAATTTCATTGCTCCAGAA

TATGCATACAAAATTGTCAAGAAAGGGGACTCAACAATTATGAAAAGTGA

ATTGGAATATGGTAACGGAAACACCAAGTGTCAAACTCCAATGGGGCGA

TAAACTCTAGCATGCCATTCCACAATATACACCCTCTCACCATTGGGGAA

TGCCCCAAATATGTGAAATCAAACAGATTAGTCCTTGCGACTGGGCTCAG

AAATAGCCCTCAAAGAGAGAGAAGAAGAAAAAAGAGAGGATTATTTGGAG

CTATAGCAGGTTTTATAGAGGGAGGATGGCAGGGAATGGTAGATGGTTGG

TATGGGTACCACCATAGCAATGAGCAGGGGAGTGGGTACGCTGCAGACAA

AGAATCCACTCAAAAGGCAATAGATGGAGTCACCAATAAGGTCAACTCGA

TCATTGACAAAATGAACACTCAGTTTGAGGCCGTTGGAAGGGAATTTAAC

AACTTAGAAAGGAGAATAGAGAATTTAAACAAGAAGATGGAAGACGGGTT

CCTAGATGTCTGGACTTATAATGCTGAACTTCTGGTTCTCATGGAAAATG

AGAGAACTCTAGACTTTCATGACTCAAATGTCAAGAACCTTTACGACAAG

GTCCGACTACAGCTTAGGGATAATGCAAAGGAGCTGGGTAACGGTTGTTT

CGAGTTCTATCATAAATGTGATAATGAATGTATGGAAAGTGTAAGAAATG

GAACGTATGACTACCCGCAGTATTCAGAAGAAGCGAGACTAAAAAGAGAG

GAAATAAGTGGAGTAAAATTGGAATCAATAGGAATTTACCAAATACTGTC

AATTTATTCTACAGTGGCGAGTTCCCTAGCACTGGCAATCATGGTAGCTG

GTCTATCCTTATGGATGTGCTCCAATGGGTCGTTACAATGCAGAATTTGC

ATTTAA

Amino Acid Sequence of Remodeled HA-1TA (SEQ ID
NO: 2):
MEKIVLLFAIVSLVKSDQICIGYRMEFFWTILKPNDAINFESNGNFIAPE

YAYKIVKKGDSTIMKSELEYGNGNTKCQTPMGAINSSMPFHNIHPLTIGE

CPKYVKSNRLVLATGLRNSPQRERRRKKRGLFGAIAGFIEGGWQGMVDGW

YGYHHSNEQGSGYAADKESTQKAIDGVTNKVNSIIDKMNTQFEAVGREFN

NLERRIENLNKKMEDGFLDVWTYNAELLVLMENERTLDFHDSNVKNLYDK

VRLQLRDNAKELGNGCFEFYHKCDNECMESVRNGTYDYPQYSEEARLKRE

EISGVKLESIGIYQILSIYSTVASSLALAIMVAGLSLWMCSNGSLQCRIC

I.
```

Another remodeled HA was designed to encompass the NH2 terminal of HA1 (D17 to P65) which includes C20 to promote disulfide bond with C483 and a portion that contributes to the formation of highly conserved epitope. This was linked to remaining portion of HAL position 241 to 346, which includes the enzymatic cleavage site and unchanged C290 to promote the formation of a disulfide bond with C58. This HA1 fragment was genetically linked to the entire HA2 fragment (G347-I568) comprising the transmembrane and cytoplasmic domains.

Figure 2:
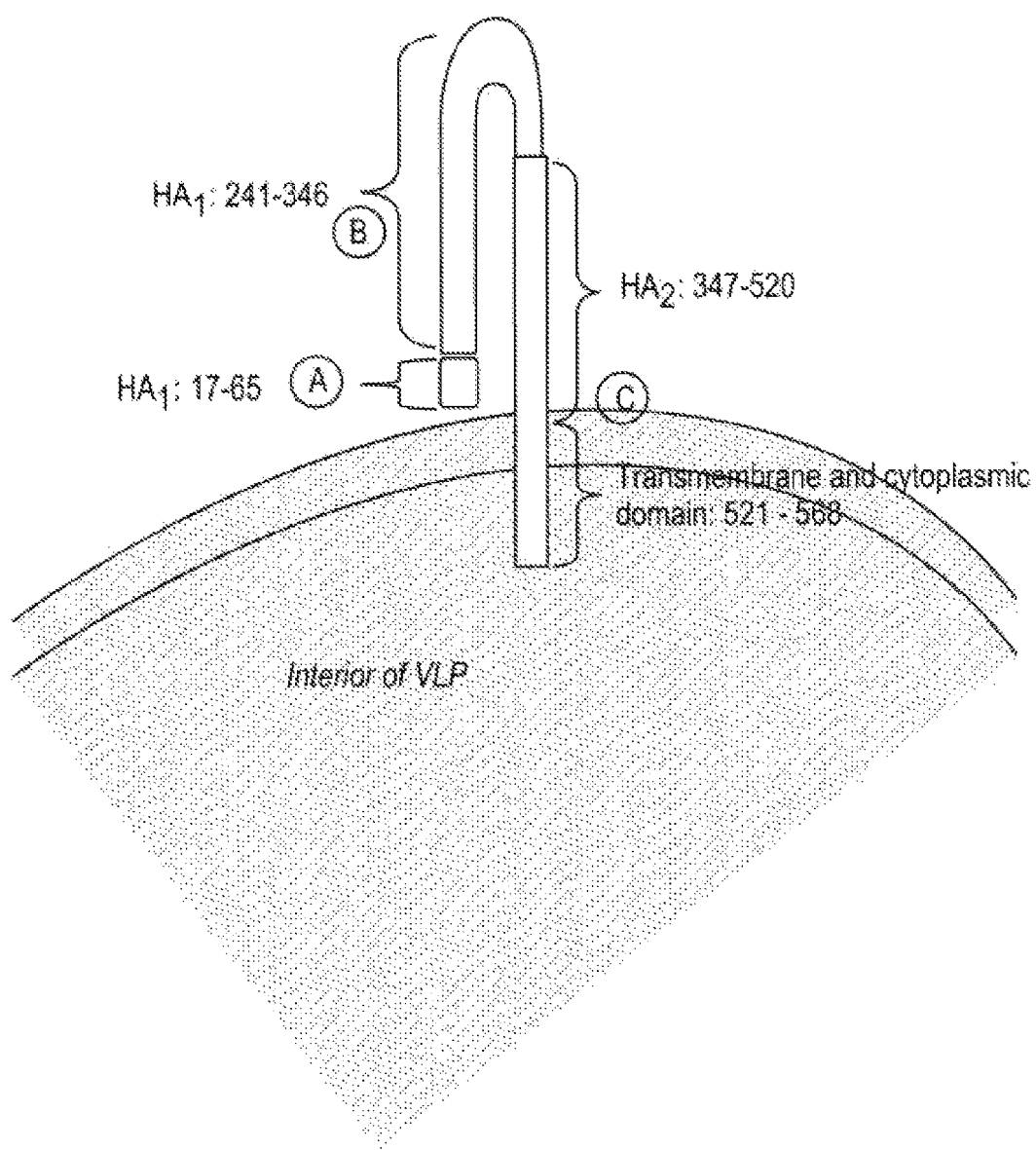

This construct was designated as remodeled HA "2TA" and depicted in FIG. 2. The DNA and amino acid sequences are shown below.

```
Nucleotide Sequence of Remodeled HA-2TA (SEQ ID
NO: 3):
ATGGAGAAAATAGTGCTTCTTTTTGCAATAGTCAGTCTTGTTAAAAGTGA

TCAGATTTGCATTGGTTACCATGCAAACAACTCGACAGAGCAGGTTGACA

CAATAATGGAAAAGAACGTTACTGTTACACATGCCCAAGACATACTGGAA

AAGAAACACAACGGGAAGCTCTGCGATCTAGATGGAGTGAAGCCTAGGAT

GGAGTTCTTCTGGACAATTTTAAAGCCGAATGATGCAATCAACTTCGAGA

GTAATGGAAATTTCATTGCTCCAGAATATGCATACAAAATTGTCAAGAAA

GGGGACTCAACAATTATGAAAAGTGAATTGGAATATGGTAACTGCAACAC

CAAGTGTCAAACTCCAATGGGGGCGATAAACTCTAGCATGCCATTCCACA

ATATACACCCTCTCACCATTGGGGAATGCCCCAAATATGTGAAATCAAAC

AGATTAGTCCTTGCGACTGGGCTCAGAAATAGCCCTCAAAGAGAGAGAAG

AAGAAAAAGAGAGGATTATTTGGAGCTATAGCAGGTTTTATAGAGGGA

GGATGGCAGGGAATGGTAGATGGTTGGTATGGGTACCACCATAGCAATGA

GCAGGGGAGTGGGTACGCTGCAGACAAAGAATCCACTCAAAAGGCAATA

GATGGAGTCACCAATAAGGTCAACTCGATCATTGACAAAATGAACACTCA

GTTTGAGGCCGTTGGAAGGGAATTTAACAACTTAGAAAGGAGAATAGAG

AATTTAAACAAGAAGATGGAAGACGGGTTCCTAGATGTCTGGACTTATAA

TGCTGAACTTCTGGTTCTCATGGAAAATGAGAGAACTCTAGACTTTCATG

ACTCAAATGTCAAGAACCTTTACGACAAGGTCCGACTACAGCTTAGGGAT

AATGCAAAGGAGCTGGGTAACGGTTGTTTCGAGTTCTATCATAAATGTGA

TAATGAATGTATGGAAAGTGTAAGAAATGGAACGTATGACTACCCGCAGT

ATTCAGAAGAAGCGAGACTAAAAAGAGAGGAAATAAGTGGAGTAAAATTG

GAATCAATAGGAATTTACCAAATACTGTCAATTTATTCTACAGTGGCGAG

TTCCCTAGCACTGGCAATCATGGTAGCTGGTCTATCCTTATGGATGTGCT

CCAATGGGTCGTTACAATGCAGAATTTGCATTTAA

Amino Acid Sequence of Remodeled HA-2TA (SEQ ID
NO: 4):
MEKIVLLFAIVSLVKSDQICIGYHANNSTEQVDTIMEKNVTVTHAQDILE

KKHNGKLCDLDGVKPRMEFFWTILKPNDAINFESNGNFIAPEYAYKIVKK

GDSTIMKSELEYGNCNTKCQTPMGAINSSMPFHNIHPLTIGECPKYVKSN

RLVLATGLRNSPQRERRRKKRGLFGAIAGFIEGGWQGMVDGWYGYHHSNE

QGSGYAADKESTQKAIDGVTNKVNSIIDKMNTQFEAVGREFNNLERRIEN

LNKKMEDGFLDVWTYNAELLVLMENERTLDFHDSNVKNLYDKVRLQLRDN

AKELGNGCFEFYHKCDNECMESVRNGTYDYPQYSEEARLKREEISGVKLE

SIGIYQILSIYSTVASSLALAIMVAGLSLWMCSNGSLQCRICI
```

Figure 3:
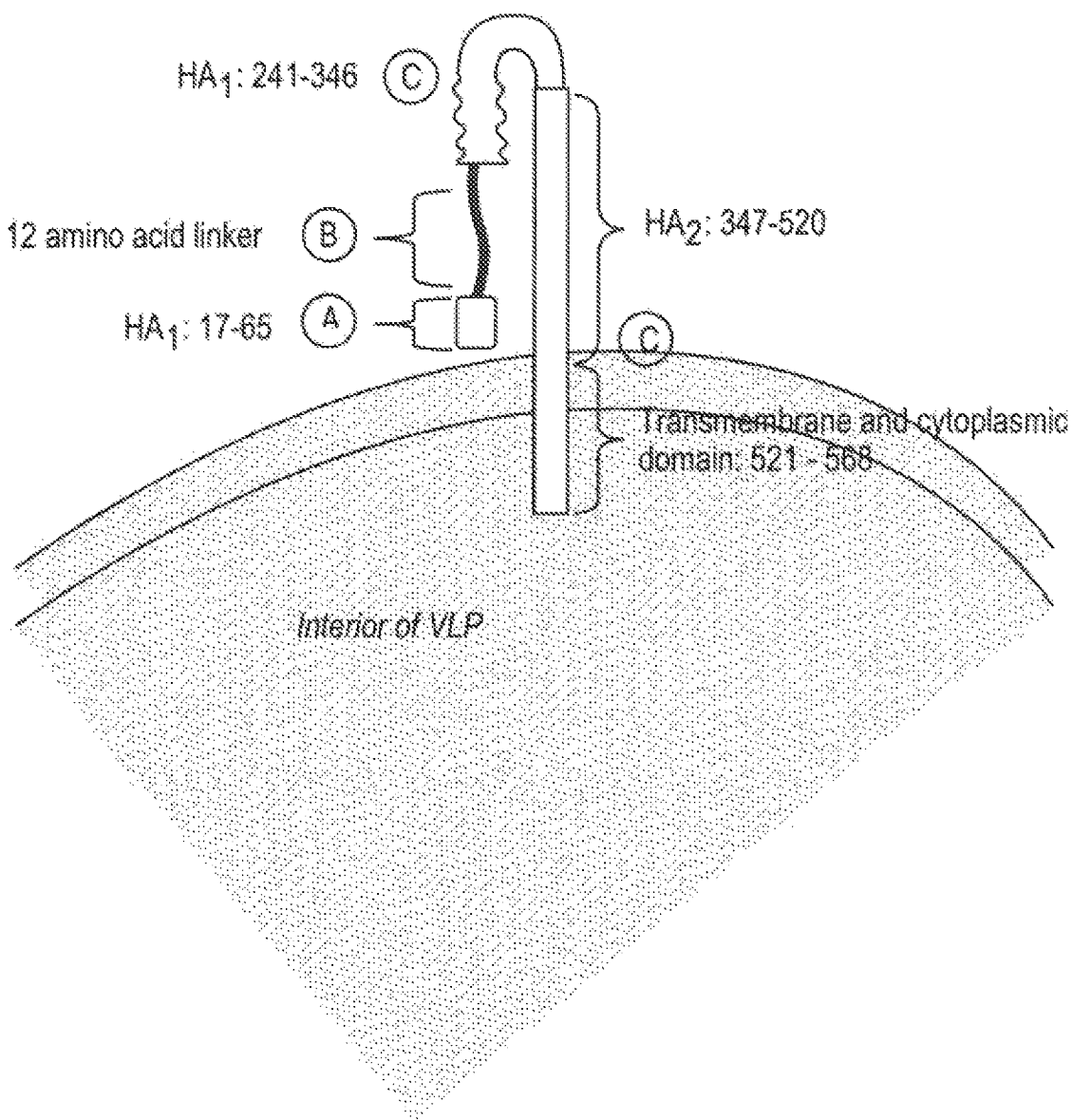

Another remodeled HA is shown in FIG. 3. This construct includes the NH2 terminal portion of the HA1 (D17 to P65), after the cleavage of the signal peptide, linked to another portion of the HA1 (M281-R346) through a designed 12aa peptide linker (DIGPGKVGYGPG, SEQ ID NO:11). In this construct, the C20-C483, C294-C318 and C58-C290 pairing residues are maintained to promote the formation of disulfide bonds. The entire HA2 region (G347 to 1568) was genetically linked to the HA1 fragment. Mutations of V412 to D412 and L419 to G419 were also introduced in HA2 to prevent protein aggregation.

This construct is identified as "3TA remodeled HA" and a schematic is shown in FIG. 3. The nucleotide and amino acid sequence of the 3TA molecule is shown below.

```
Nucleotide Sequence of Remodeled HA-3TA (SEQ ID
NO: 5):
ATGGAGAAAATAGTGCTTCTTTTTGCAATAGTCAGTCTTGTTAAAAGTGA

TCAGATTTGCATTGGTTACCATGCAAACAACTCGACAGAGCAGGTTGACA

CAATAATGGAAAAGAACGTTACTGTTACACATGCCCAAGACATACTGGAA

AAGAAACACAACGGGAAGCTCTGCGATCTAGATGGAGTGAAGCCTGACAT

AGGACCAGGAAAGGTAGGATACGGACCAGGAATGAAAAGTGAATTGGAA

TATGGTAACTGCAACACCAAGTGTCAAACTCCAATGGGGGCGATAAACTC

TAGCATGCCATTCCACAATATACACCCTCTCACCATTGGGGAATGCCCCA

AATATGTGAAATCAAACAGATTAGTCCTTGCGACTGGGCTCAGAAATAGC

CCTCAAAGAGAGAAGAAGAAAAAGAGAGGATTATTTGGAGCTATAG

CAGGTTTTATAGAGGGAGGATGGCAGGGAATGGTAGATGGTTGGTATGGG

TACCACCATAGCAATGAGCAGGGGAGTGGGTACGCTGCAGACAAAGAAT

CCACTCAAAAGGCAATAGATGGAGTCACCAATAAGGTCAACTCGATCATT

GACAAAATGAACACTCAGTTTGAGGCCGACGGAAGGGAATTTAACAACG

GAGAAAGGAGAATAGAGAATTTAAACAAGAAGATGGAAGACGGGTTCCT

AGATGTCTGGACTTATAATGCTGAACTTCTGGTTCTCATGGAAAATGAGA

GAACTCTAGACTTTCATGACTCAAATGTCAAGAACCTTTACGACAAGGTC

CGACTACAGCTTAGGGATAATGCAAAGGAGCTGGGTAACGGTTGTTTCGA

GTTCTATCATAAATGTGATAATGAATGTATGGAAAGTGTAAGAAATGGAA

CGTATGACTACCCGCAGTATTCAGAAGAAGCGAGACTAAAAAGAGAGGA

AATAAGTGGAGTAAAATTGGAATCAATAGGAATTTACCAAATACTGTCAA

TTTATTCTACAGTGGCGAGTTCCCTAGCACTGGCAATCATGGTAGCTGGT

CTATCCTTATGGATGTGCTCCAATGGGTCGTTACAATGCAGAATTTGCAT

TTAA

Amino Acid Sequence of Remodeled HA-3TA (SEQ ID
NO: 6):
MEKIVLLFAIVSLVKSDQICIGYHANNSTEQVDTIMEKNVTVTHAQDILE

KKHNGKLCDLDGVKPDIGPGKVGYGPGMKSELEYGNCNTKCQTPMGAINS

SMPFHNIHPLTIGECPKYVKSNRLVLATGLRNSPQRERRRKKRGLFGAIA

GFIEGGWQGMVDGWYGYHHSNEQGSGYAADKESTQKAIDGVTNKVNSIID

KMNTQFEADGREFNNGERRIENLNKKMEDGFLDVWTYNAELLVLMENERT

LDFHDSNVKNLYDKVRLQLRDNAKELGNGCFEFYHKCDNECMESVRNGTY

DYPQYSEEARLKREEISGVKLESIGIYQILSIYSTVASSLALAIMVAGLS

LWMCSNGSLQCRICI
```

Figure 4:
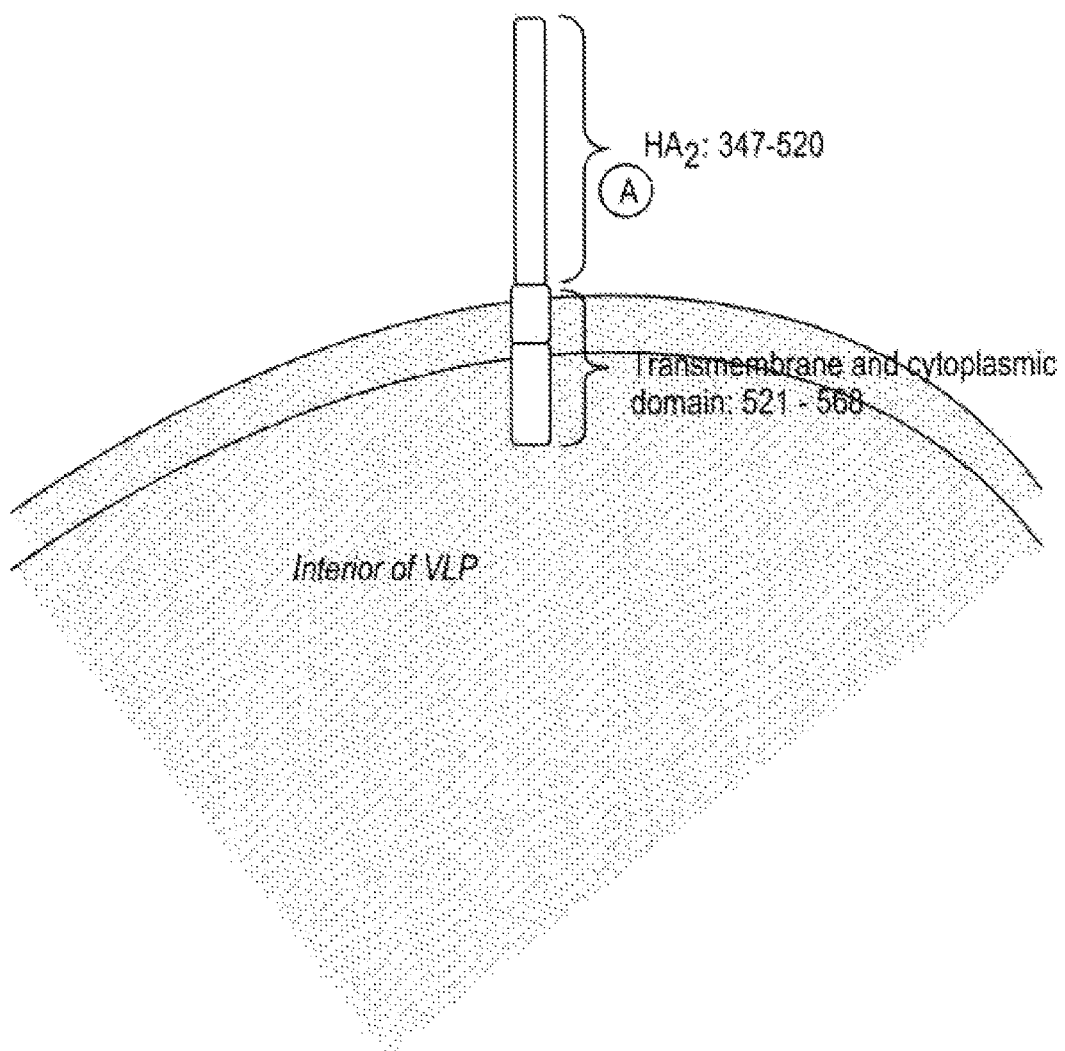

Another example of a modified influenza HA is shown in FIG. 4 (designated "4TA"). This construct includes an HA2 fragment (including the extracellular region (residues 347-520) and transmembrane and cytoplasmic domains (residues 521-568) domains linked to the secretion signal peptide. The signal peptide is removed during transcription/translocation and it is not present in the HA2 structure incorporated onto the VLP vaccine (as is the case for the other remodeled HAs). In addition, the transmembrane domain and cytoplasmic tail at the carboxyl terminal of the HA2 subunits are optionally replaced with analogous sequences of an influenza virus from which the M1 protein is derived or the sequence that best interacts with an M1 analogue. Optimizing these molecular contacts enhances particle assembly and release. The nucleotide and amino acid sequence of the 4TA molecule is shown below.

```
Nucleotide Sequence of Remodeled HA-4TA (SEQ ID
NO: 7):
ATGGAGAAAATAGTGCTTCTTTTTGCAATAGTCAGTCTTGTTAAAAGTGG

ATTATTTGGAGCTATAGCAGGTTTTATAGAGGGAGGATGGCAGGGAATGG

TAGATGGTTGGTATGGGTACCACCATAGCAATGAGCAGGGGAGTGGGTAC

GCTGCAGACAAAGAATCCACTCAAAAGGCAATAGATGGAGTCACCAATAA

GGTCAACTCGATCATTGACAAAATGAACACTCAGTTTGAGGCCGTTGGAA

GGGAATTTAACAACTTAGAAAGGAGAATAGAGAATTTAAACAAGAAGAT

GGAAGACGGGTTCCTAGATGTCTGGACTTATAATGCTGAACTTCTGGTTC

TCATGGAAAATGAGAGAACTCTAGACTTTCATGACTCAAATGTCAAGAAC

CTTTACGACAAGGTCCGACTACAGCTTAGGGATAATGCAAAGGAGCTGGG

TAACGGTTGTTTCGAGTTCTATCATAAATGTGATAATGAATGTATGGAAA

GTGTAAGAAATGGAACGTATGACTACCCGCAGTATTCAGAAGAAGCGAGA

CTAAAAAGAGAGGAAATAAGTGGAGTAAAATTGGAATCAATAGGAATTTA

CCAAATACTGTCAATTTATTCTACAGTGGCGAGTTCCCTAGCACTGGCAA

TCATGGTAGCTGGTCTATCCTTATGGATGTGCTCCAATGGGTCGTTACAA

TGCAGAATTTGCATTTAA

Amino Acid Sequence of Remodeled HA-4TA (SEQ ID
NO: 8):
MEKIVLLFAIVSLVKSGLFGAIAGFIEGGWQGMVDGWYGYHHSNEQGSGY

AADKESTQKAIDGVTNKVNSIIDKMNTQFEAVGREFNNLERRIENLNKKM

EDGFLDVWTYNAELLVLMENERTLDFHDSNVKNLYDKVRLQLRDNAKELG

NGCFEFYHKCDNECMESVRNGTYDYPQYSEEARLKREEISGVKLESIGIY

QILSIYSTVASSLALAIMVAGLSLWMCSNGSLQCRICI
```

Figure 5A:
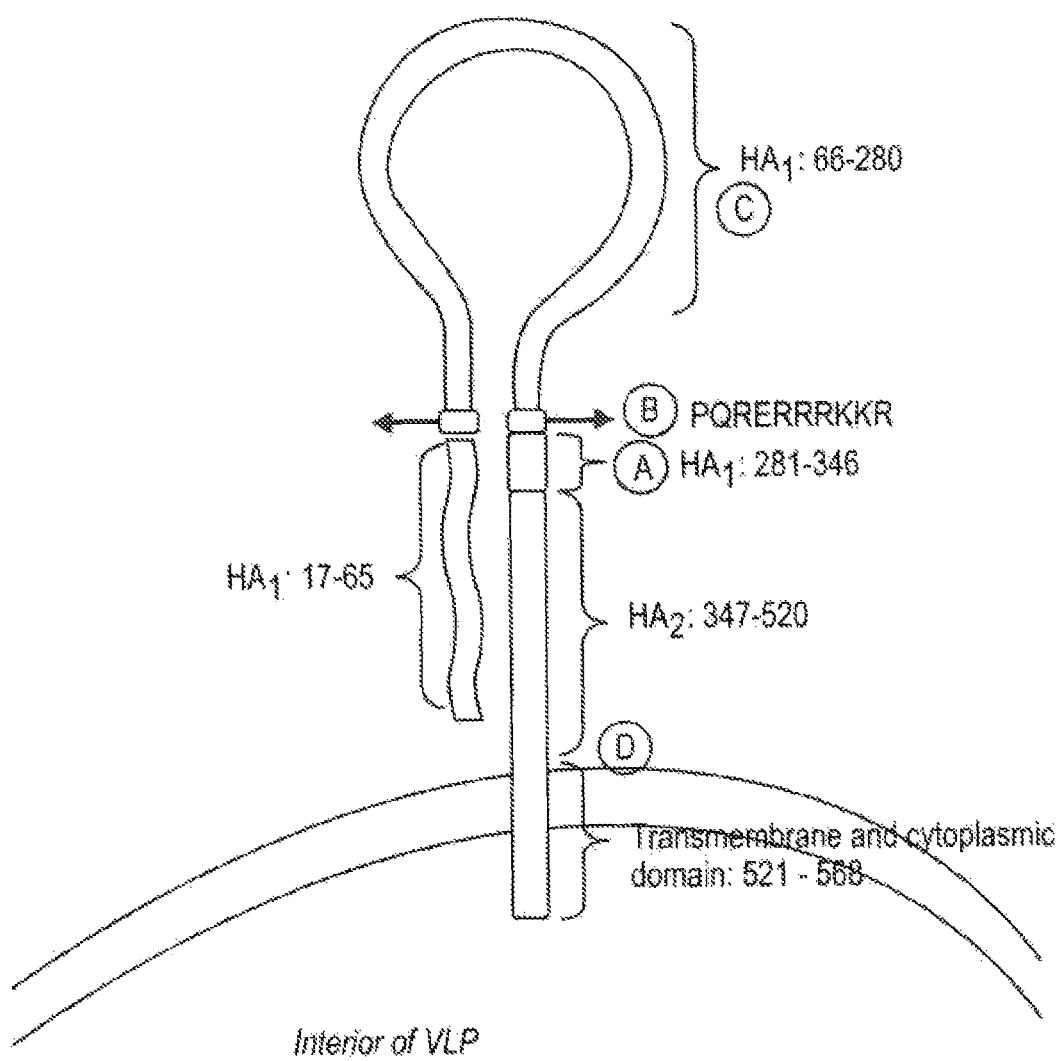
Figure 5B:
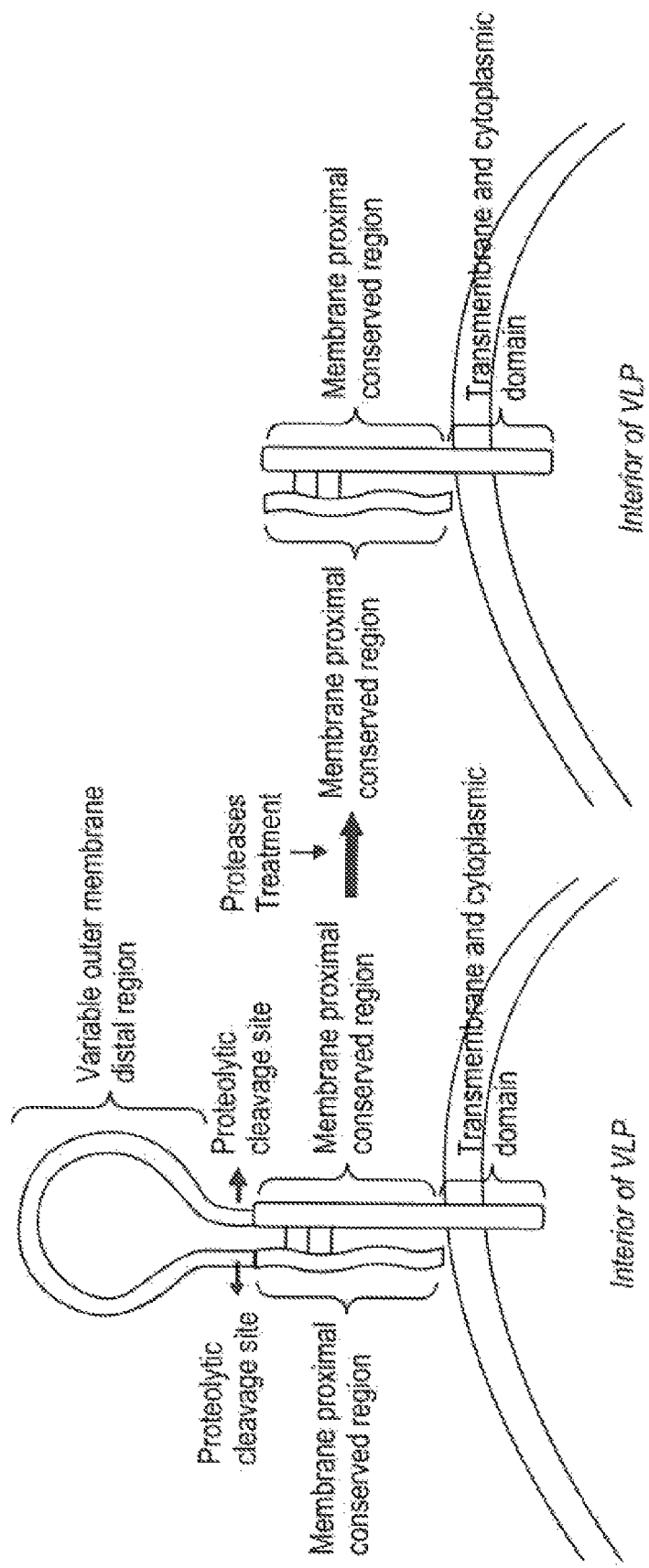

In another example, an influenza HA polypeptide is remodeled by inserting one or more cleavage sites within the sequence of the protein. As shown in FIG. 5A (designated "5TA"), exemplary insertion sites include is between P65 and L66 and/or between I280 and M281. FIG. 5 also shows an exemplary cleavage site of 12 residues (e.g., 12-mers multi basic proteolytic cleavage sites). An additional change includes mutation of 3 residues in the native proteolytic cleavage site (KKR to GGG) can also be included in order to prevent cleavage at this location. Proteases treatment of this molecule (see FIG. 5B) removes the globular head of the HA exposing the conserved epitopes formed by the HA2 stem and remaining portions of HA1 The nucleotide and amino acid sequences of the 5TA molecule are shown below.

```
Nucleotide Sequence of Remodeled HA-5TA (SEQ ID
NO: 9):
ATGGAGAAAATAGTGCTTCTTTTTGCAATAGTCAGTCTTGTTAAAAGTGA
TCAGATTTGCATTGGTTACCATGCAAACAACTCGACAGAGCAGGTTGACA
CAATAATGGAAAAGAACGTTACTGTTACACATGCCCAAGACATACTGGAA
AAGAAACACAACGGGAAGCTCTGCGATCTAGATGGAGTGAAGCCTCCACA
GAGAGAAAGAAGAAGAAAGAAGAGACTAATTTTGAGAGATTGTAGCGTA
GCTGGATGGCTCCTCGGAAACCCAATGTGTGACGAATTCATCAATGTGCC
GGAATGGTCTTACATAGTGGAGAAGGCCAATCCAGTCAATGACCTCTGTT
ACCCAGGGGATTTCAATGACTATGAAGAATTGAAACACCTATTGAGCAGA
ATAAACCATTTTGAGAAAATTCAGATCATCCCCAAAAGTTCTTGGTCCAG
TCATGAAGCCTCATTAGGGGTGAGCTCAGCATGTCCATACCAGGGAAAGT
CCTCCTTTTTCAGAAATGTGGTATGGCTTATCAAAAAGAACAGTACATAC
CCAACAATAAAGAGGAGCTACAATAATACCAACCAAGAAGATCTTTTGGT
ACTGTGGGGGATTCACCATCCTAATGATGCGGCAGAGCAGACAAAGCTCT
ATCAAAACCCAACCACCTATATTTCCGTTGGGACATCAACACTAAACCAG
AGATTGGTACCAAGAATAGCTACTAGATCCAAAGTAAACGGGCAAAGTGG
AAGGATGGAGTTCTTCTGGACAATTTTAAAGCCGAATGATGCAATCAACT
TCGAGAGTAATGGAAATTTCATTGCTCCAGAATATGCATACAAAATTGTC
AAGAAAGGGGACTCAACAATTCCACAGAGAGAAAGAAGAAGAAAGAAGA
GAATGAAAGTGAATTGGAATATGGTAACTGCAACACCAAGTGTCAAACT
CCAATGGGGCGATAAACTCTAGCATGCCATTCCACAATATACACCCTCT
CACCATTGGGGAATGCCCCAAATATGTGAAATCAAACAGATTAGTCCTTG
CGACTGGGCTCAGAAATAGCCCTCAAAGAGAGAGAAGAAGAAAGAAGAG
AGGATTATTTGGAGCTATAGCAGGTTTTATAGAGGGAGGATGGCAGGGAA
TGGTAGATGGTTGGTATGGGTACCACCATAGCAATGAGCAGGGGAGTGGG
TACGCTGCAGACAAAGAATCCACTCAAAAGGCAATAGATGGAGTCACCA
ATAAGGTCAACTCGATCATTGACAAAATGAACACTCAGTTTGAGGCCGTT
GGAAGGGAATTTAACAACTTAGAAAGGAGAATAGAGAATTTAAACAAGA
AGATGGAAGACGGGTTCCTAGATGTCTGGACTTATAATGCTGAACTTCTG
GTTCTCATGGAAAATGAGAGAACTCTAGACTTTCATGACTCAAATGTCAA
GAACCTTTACGACAAGGTCCGACTACAGCTTAGGGATAATGCAAAGGAGC
TGGGTAACGGTTGTTTCGAGTTCTATCATAAATGTGATAATGAATGTATG
GAAAGTGTAAGAAATGGAACGTATGACTACCCGCAGTATTCAGAAGAAGC
GAGACTAAAAGAGAGGAAATAAGTGGAGTAAAATTGGAATCAATAGGA
ATTTACCAAATACTGTCAATTTATTCTACAGTGGCGAGTTCCCTAGCACT
GGCAATCATGGTAGCTGGTCTATCCTTATGGATGTGCTCCAATGGGTCGT
TACAATGCAGAATTTGCATTTAA
```

Amino Acid Sequence of Remodeled HA-5TA (SEQ ID NO: 10):
MEKIVLLFAIVSLVKSDQICIGYHANNSTEQVDTIMEKNVTVTHAQDILE
KKHNGKLCDLDGVKPPQRERRRKKRLILRDCSVAGWLLGNPMCDEFINVP
EWSYIVEKANPVNDLCYPGDFNDYEELKHLLSRINHFEKIQIIPKSSWSS
HEASLGVSSACPYQGKSSFFRNVVWLIKKNSTYPTIKRSYNNTNQEDLLV
LWGIHHPNDAAEQTKLYQNPTTYISVGTSTLNQRLVPRIATRSKVNGQSG
RMEFFWTILKPNDAINFESNGNFIAPEYAYKIVKKGDSTIPQRERRRKKR
MKSELEYGNCNTKCQTPMGAINSSMPFHNIHPLTIGECPKYVKSNRLVLA
TGLRNSPQRERRRKKRGLFGAIAGFIEGGWQGMVDGWYGYHHSNEQGSGY
AADKESTQKAIDGVTNKVNSIIDKMNTQFEAVGREFNNLERRIENLNKKM
EDGFLDVWTYNAELLVLMENERTLDFHDSNVKNLYDKVRLQLRDNAKELG
NGCFEFYHKCDNECMESVRNGTYDYPQYSEEARLKREEISGVKLESIGIY
QILSIYSTVASSLALAIMVAGLSLWMCSNGSLQCRICI These remodeled structures typically lack a large portion of the HA1 domain, deleting the majority of the immunodominant epitopes but maintaining a small NH2 terminal region containing the translocation signal sequence which is linked to alternative configurations of HA1 and HA2 subunits. The specific modifications of the HA molecule are performed at the DNA level and subsequently sub-clone together with the combination of genes required for VLP assembly.

Synthesis of the modified HA gene alone or together with the M1 (or a functionally analogous matrix protein), M2, NA and NP together or in combinations in a eukaryotic expression system leads to the production of vesicular particles or virus-like particles (VLPs) displaying an array of modified HA molecules on their surface. The structure of the modified HA raises the antigenic profile of the conserved subdominant epitopes which in this configuration are able to trigger a strong and broadly protective immune response against a variety of influenza virus subtypes and antigenic variants.

Therefore, this vaccine affords a comprehensive protection that prevails over emerging mutants prolonging its efficacy. As described in detail above, a variety of ways to produce and evaluate the appropriate VLPs are known to one knowledgeable in the art. For example, the genes required for VLP formation, including the DNA sequences coding for the modified HA can be expressed in eukaryotic cells. Alternative recombinant expression systems are used for the production of VLPs which include but are not limited to baculovirus/insect cell systems, transiently or stably transfected mammalian, yeast, plant cells or prokaryotic cells using plasmids, vectors, viruses or other methods for the introduction and expression of single or multiple genes into cells. Produced VLPs are tested for reactivity with antibodies that recognize immunodominant and subdominant regions. VLP structures carrying modified HAs that react with antibodies recognizing conserved subdominant epitopes are used to immunize animals and evaluate the capacity of the sera to neutralize wild type intact virus as well as the ability to elicit a broadly protective immune response against challenge viruses in mice and ferrets.

Also as described above, immunization of humans or other species susceptible to influenza with the described VLP vaccine (formulated with VLPs assembled with modified HAs as described herein of type A and B viruses) will elicit a broadly neutralizing immune response capable of protecting against subtypes and antigenic variants of the type A as well as type B influenza viruses and their antigenic variants.

Example 2: Generation of Mammalian DNA Plasmid Vectors or Recombinant Baculovirus Carrying Multiple Genes for the Production of Virus-Like Particles (VLP) Displaying Unique HA Molecules In this example, we describe generation of constructs required for the production of VLPs. The general structure of the constructs generated is shown in FIG. 6. The genes of interest were subcloned into mammalian plasmids (vectors, FIG. 6, panel I) containing unique regulatory sequences that enhance not only high and sustainable levels of gene expression but also the rate of generating stably transfected cells. An alternative method of VLP production is the utilization of the baculovirus-insect cells expression system. The overall structure of constructs generated is depicted in FIG. 6 panel II.

The influenza M1 and M2 genes were sequentially subcloned into a mammalian plasmid expression vector using the appropriate restriction sites such that each gene was under the transcriptional control of a mammalian promoters (CMV promoter or promoter A). In addition, the plasmids into which the influenza M1 and M2 genes were cloned also contained an antibiotic selection markers (e.g., hygromicin, puromycin, or neomycin) and specific sequences upstream of each gene that maintain an open chromatin state following DNA integration within mammalian chromosomes. Thus, these constructs are suitable for the performance of transient or stably protein expression experiment.

Figure 9A:
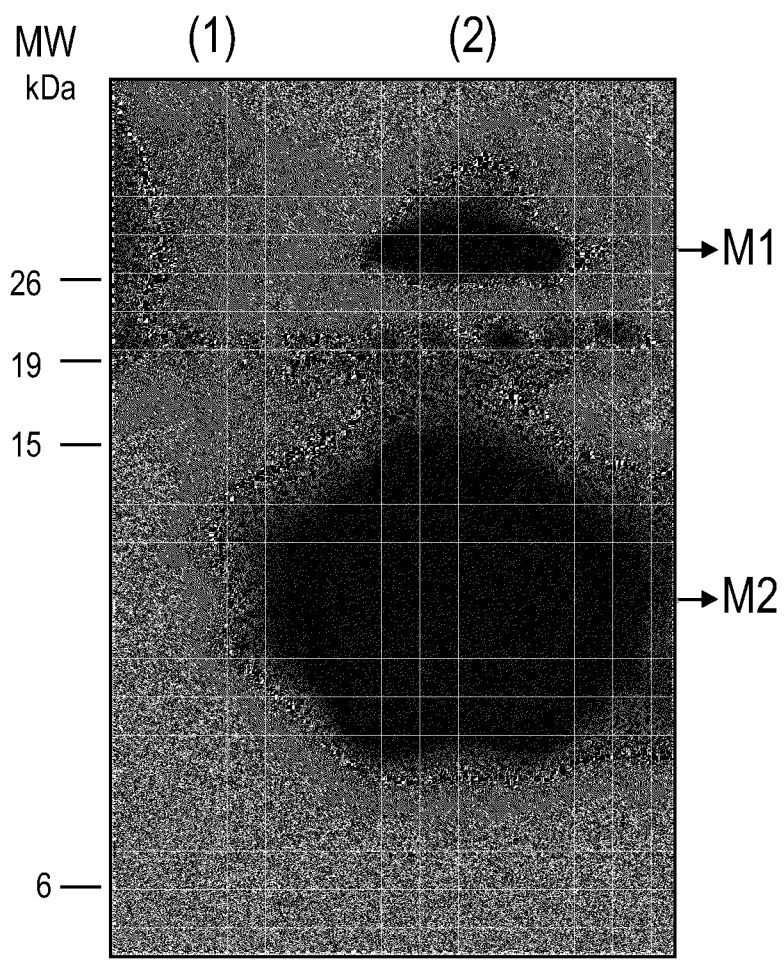

An example of selection of stably transfected mammalian cells using fluorescence cell sorting is shown in FIG. 8A-C. Furthermore, the level of expression of M1/M2 proteins in stably transfected MDCK and CHO cells are shown in FIGS. 9A and B, respectively.

The remodeled HA and NA genes were subcloned into another mammalian plasmid expression vector using the appropriate restriction sites such that each gene was under the transcriptional control of a mammalian promoters (CMV promoter or promoter A).

After completion of each construct, the genes orientation and integrity were verified by restriction enzyme analysis and sequencing. Plasmid DNA of each construct was further amplified by transforming MAX Efficiency Stbl2 competent *E. Coli* cells, and performing maxi-prep DNA preparation (Qiagen, Valencia, Calif.). The concentration of plasmid DNAs were determined by spectrophotometry. Transient transfections were performed utilizing circular DNA, whereas transfections for the generation of stable cell lines were carried out with linear DNA cut with I-SceI restriction enzyme.

A baculovirus transfer vector was generated for VLP production in insect cells. The four influenza genes were subcloned within a single plasmid and under the transcriptional control of baculovirus promoters as illustrated in FIG. 6 panel II. As previously described, the genes orientation and integrity were verified by restriction enzyme analysis and sequencing. Plasmid DNA was further amplified by performing maxi-prep DNA preparation. Co-transfection of the transfer vector (carrying the four influenza genes) together with linearized baculovirus DNA into Sf9 insect cells results in the creation of recombinant baculovirus for the production of VLP vaccines.

Example 3: Transfection of DNA Plasmids into Mammalian Cells by Electroporation Following generation of the desired vectors as described in Example 2, the vectors were utilized for the production of VLPs in mammalian cells (CHO, Vero, MDCK, WI-38 or MRCS).

To generate stably transfected cells linearized DNA was introduced to cell by electroporation. Briefly, 24 hours prior to DNA electroporation, selected cells were seeded into a T-175 flask at a concentration of ~4 million cells allowing for the formation of an 80-85% confluent monolayer in 24 hours. Prior to electroporation, the cell monolayer was washed once with 8 ml of 1× PBS (Gibco) then treated with 4 ml of 1× trypsin-EDTA (Gibco) and incubate for 5 minutes at 37° C. Cells were resuspended by adding to the flask 6 ml of DMEM (Gibco) containing 10% FBS (Invitrogen, San Diego, Calif.) collected in a tube and subsequently pelleted by centrifugation at 500×g for 5 minutes. Cell pellet was washed twice with 5 ml of ice cold 1× RPMI 1640 (Cellgro, Mediatech, Manassas, Va.) and then resuspend in 500 µl of ice cold 1× RPMI.

The cell suspension received 6 µg of linearized plasmid expressing M1/M2, or M1/M2 plus a plasmid expressing NA/remodeled HA, gently mixed by pipeting and then transferred into a 0.4 cm gap electroporation cuvette (Bio-Rad, Hercules, Calif.). The cuvette was placed in a Bio-Rad Gene Pulsar, and cells electroporated using the following parameters: 400V, 960µF. Electroporated cells were kept at room temperature for 5 minutes, then transferred into a 6-well plate in DMEM with 10% FBS and penicillin/streptomycin (Gibco) and incubated at 37° C. with 5% CO2. Six hours post electroporation, the medium was aspirated, cells washed once with 1×PBS, and fresh medium added. Cells were incubated at 37° C. with 5% $CO_2$ until antibiotic selection was initiated.

A modified protocol was used for the electroporation of suspension cells, e.g. CHO cell line. Cells were directly collected from the culture vessel without the need of trypsin treatment. Subsequent steps were performed as described above.

Example 4: Transfection of DNA Plasmids into Mammalian Cells by Chemical Methods Mammalian cells (CHO, Vero, MDCK, MRCS or WI-38) were prepared for transfection by plating in an appropriate culture vessel (25 cm2 flasks for CHO cells or 75 cm2 flasks for Vero, MDCK, MRCS or WI-38 cells) at a density of $1.5 \times 10^6$ to $2.5 \times 10^6$ cells/ml in 5 ml of CHO-S-SFM II medium (CHO cells) or 10 ml of DMEM (Vero, MDCK, MRCS, WI-38) supplemented with 5% fetal bovine serum (FBS) (Invitrogen, Carlsbad, Calif.). Adherent cells (Vero, MDCK, MRCS, WI-38) were plated 24 hours prior to the initiation of the transfection procedure.

Following this step, a DNA-lipid complexing reaction comprising of plasmid DNA with lipofectamine was set up. The plasmid DNA of interest or mixture thereof was diluted in 500 µl of Opti-MEM medium in one tube and 20 µl of lipofectamine 2000 was diluted in 480 µl of Opti-MEM medium (Invitrogen, Carlsbad, Calif.) in another tube. The lipofectamine-OptiMEM mixture was incubated at room temperature for 5 minutes.

After this step, the plasmid DNA-OptiMEM mixture was combined with the lipofectamine-OptiMEM mixture and the reaction was allowed to proceed at room temperature for 20 minutes. The DNA-lipofectamine complex was then added to the cells previously plated as described above. In the case of CHO cells, five hours after the addition of the DNA-lipofectamine complex, 2.5 ml of the contents of the 25 cm2 flask was transferred to another 25 cm2 flask and 4.5 ml of CHO-S-SFM II medium was added to both flasks. Adherent cells were kept in the culture flask and 5 ml of fresh media was added. None of the reagents or media used in the transfection process contained any antibiotics as these could get delivered to the interior of the cells by getting incorporated in the DNA-lipid complex which could prove toxic to the cells.

For the transient expression of the proteins of interest to create VLPs, the plasmids were introduced into the cells in the form of a DNA-lipid complex in which the DNA is in its native circular form. Expression of the VLP proteins in the transfected cell lysate and in the culture supernatant was evaluated 72-96 hours post-transfection.

To generate stably transfected cells, in which the plasmid/s of interest are integrated with the chromosomal cellular DNA establishing an state of continuous protein expression, the transfection procedure was followed with the exception that the plasmid/s introduced into the cells were in a linear configuration. The plasmids into which the genes of interest were cloned also contain antibiotic resistance markers e.g. Hygromycin, Puromycin or Neomycin. Thus, after 48-96 hours post transfection, cells were subjected to selection by adding to the culture medium the antibiotic of choice based on the resistance gene delivered by the plasmid. Following 8-10 days of selection, cells that grew in the presence of the antibiotic were isolated based on the expression and detection of surface protein/s using fluorescence-activated cell sorting (FACS).

Example 5: Transfection of Circular DNA for Transient Expression of Protein and Assembly of VLPs Displaying Remodeled HA Assessment of VLPs production was performed by introducing a combination of uncut circular plasmid to mammalian cells by either electroporation or chemical transfections. In this example the M1/M2 vector was combined with a NA/HA (remodeled, FIG. 1) and delivered to mammalian cells (CHO, MDCK, MRCS or WI-38) by either of the two transfection methods described.

Western blot analysis of cell lysates, culture supernatant and concentrated purified supernatant demonstrated that these proteins were expressed in the cells and released into the culture media as shown in FIG. 10. Furthermore, concentrated and purified material produced and released for these cells was examined by negative staining electron microscopy and cryo-electron microscopy. These studies revealed the presence of virus-like particles which resemble enveloped virus particles such as the influenza virus (FIG. 11).

Example 6: Transfection of Linearized DNA to Generate Stably Transfected Mammalian Cells Transfection of linearized plasmid DNA into mammalian cells leads to plasmid integration into the host cell genome. Delivery of linear forms of any of the constructs described in Example 1 leads to plasmid integration and subsequent expression the genes carried by the vector DNA. This strategy allows for the creation of stably transfected cell lines that constitutively express the gene product/s of interest.

Pursuing this approach, a linearized M1/M2 vector (FIG. 6A) was introduced by electroporation or chemical transfection into MDCK, Vero or CHO cells. After this step, cells were treated with one antibiotic (hygromicin, puromycin or neomycin) chosen based on the antibiotic resistance gene carried by the plasmid. The M1/M2 vector contains the hygromycin resistance gene, thus cells transfected with this plasmid were treated with this antibiotic to select stably transfected cell lines. Cells that grew in the presence of the antibiotic were tested for the expression of the M2 protein on their surface and cloned using fluorescence activated cell sorting (FACS).

FIG. 8 shows FACS histogram of M1/M2 transfected CHO cells which demonstrated that fraction of cell population expressed the M2 protein. Multiple cell clones were expanded and the expression of both M1 and M2 proteins further evaluated by Western blot.

Furthermore, as shown in FIGS. 9A and B selected M1/M2 stably transfected MDCK and CHO cell lines constitutively express these proteins. These cell lines can be transfected with a vector carrying NA/HA (remodeled) for the assembly and release of influenza virus-like particles displaying unique HA molecules (FIG. 1-5).

Example 7: Selection of Stably Transfected Mammalian Cells

Mammalian cells that had been transfected with linearized plasmids encoding gene(s) of interested were then subjected to antibiotic treatment to select out the cells in which the transfected plasmid had integrated into the host cell genome. The transfected plasmid contains an antibiotic resistance cassette which confers resistance to either hygromycin, puromycin or neomycin.

About 48-72 hours post-transfection cells were subjected to selection pressure by adding the appropriate concentration of antibiotic (400 ug/ml of hygromycin, 10 ug/ml of puromycin or 10 ug/ml of neomycin) to the cell culture medium and sub-culturing the transfected cells in this medium through several cell passages. This process allowed the survival of only those cells into which chromosomal integration of the genes from the transfected plasmid has taken place and were selected out from the rest of the population.

Example 8: Fluorescence Activated Cell Sorting (FACS) Analysis of M1/M2 Transfected Cells Cells obtained as described above were harvested from the tissue culture flasks and washed three times by consecutive centrifugation at 500×g for 5 min followed by re-suspension in phosphate buffered saline (PBS). After the third wash, cells were counted and divided into three aliquots of $5\times10^6$ cells each. One aliquot, the one which was going to be sorted for cell surface M2 expression, was incubated with an anti-M2 monoclonal antibody (Abcam Inc, Cambridge, Mass.) at a dilution of 1:500 in PBS for 1 hour at room temperature. The second aliquot was incubated with a monoclonal antibody to influenza A nucleoprotein (Meridian Life Sciences, Saco, Me.) at a dilution of 1:200 in PBS for 1 hour at room temperature. This aliquot served as an isotype control for the flow cytometry experiment. The third aliquot served as the unstained control for the experiment.

After the incubation with the respective antibodies, the cells were washed with PBS three times and incubated with a Fluorescein isothiocyanate (FITC) labeled anti-mouse antibody (Abcam Inc, Cambridge, Mass.) at a dilution of 1:100 in PBS for 1 hr at room temperature. After these treatments, the cells were washed three times with PBS and re-suspended in a final volume of 3 ml of cell culture medium. These samples were then analyzed in a MoFlo cell sorter.

Cells that expressed high levels of M2 protein on their cell surface, as determined by their specific green fluorescence spectrum were sorted as 1 cell/well into 96 well plates that contained 100 µl of cell culture medium in each well. FIG. 8 depicts a sorting experiment performed with M1/M2 transfected cells.

Figure 7B:
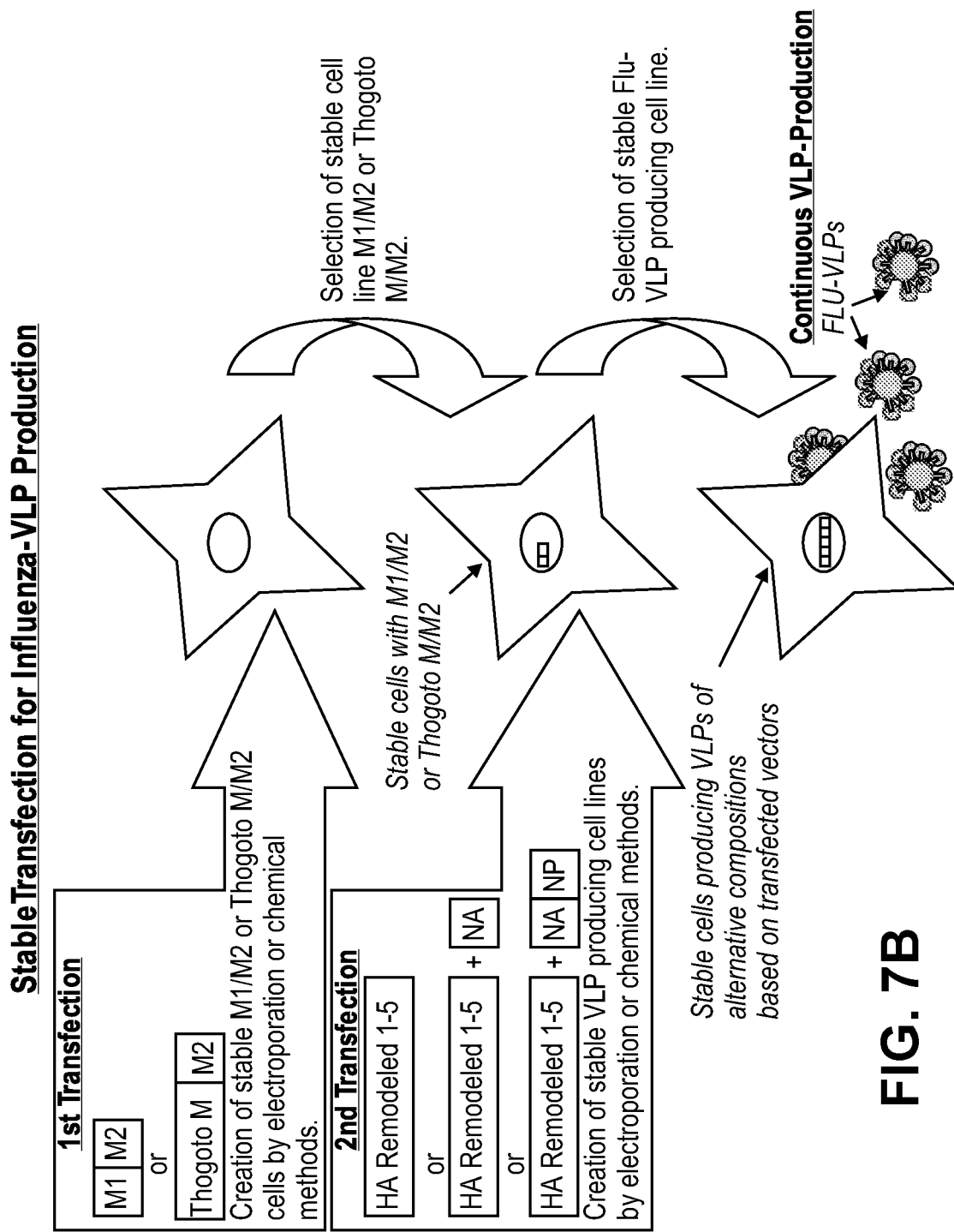

This selection method is applied for the identification and isolation of cells transfected with any the constructs described herein (e.g., FIGS. 1-5). Cells transfected with the DNA vector carrying the NA/HA remodeled 1 (FIG. 1) express both NA and HA proteins, which are displayed on the cell surface allowing for the identification and isolation of stably transfected clones that continuously express these proteins. Selection via HA uses a broadly neutralizing monoclonal antibody that recognizes a conserved epitope on remodeled HA molecule. Following the creation of the first stably transfected cell line, a second transfection is performed to introduce and integrate another set of genes into the host genome of the basic cell line. This strategy is depicted in FIG. 7B, and identification and selection of stably cell lines generated on the second round of transfections is also performed by FACS analysis. The five constructs of remodeled HA with or without NA which are delivered by the vector constructs depicted on FIG. 6 (constructs shown in panels I) are surface molecules and displayed on the cell membrane, therefore suitable for the FACS strategy to identify and selected stably transfected cell lines that continuously produce VLPs with remodeled HA molecules.

Example 9: End-Point Cloning and Expansion of a Stably Transfected and Constitutively Producing M1 and M2 Influenza Proteins To obtain clonal cell lines from the stably transfected cell population, end point cloning was performed. The cells were harvested and counted using a hemocytometer. The cells were then diluted in an appropriate volume of culture medium such that the final concentration reached 10 cells per ml. This cell preparation was gently agitated to ensure homogenous cell distribution and then plated into sterile 96 well plates at 100 µl/well. The plates were then incubated at 37° C. with a humidified atmosphere of 5% CO2 and monitored regularly for clonal cell growth. Wells with actively growing cells were identified over a period of time. When the clonal cells in these wells reached about 70-80% confluency they were scaled up by sequential passages to 6 well plates, 25 cm$^2$ and 75 cm$^2$ flasks.

Example 10: Analysis of Protein Expression

Analysis of protein expression was carried out on cell pellets and on supernatants of transfected mammalian cells. Tranfected cells were harvested, washed with 1×PBS and resuspended in RIPA buffer [Tris-HCl (pH 7.4) 50 mM, Sodium Chloride 150 mM, EDTA 1 mM, Triton X-100 1%, NP-40 1%, Sodium dodecyl sulfate 0.1%] and then disrupted by freezing and thawing cycles and pipeting and finally stored at −20° C. until further used. The total protein concentration in each sample was estimated by the Bradford method; briefly, 10 µl of the sample is added to 1.0 ml of 1× Bradford Dye reagent (Bio-Rad Inc., Hercules, Calif.) which was pre-warmed to room temperature. This reaction mixture is then shaken vigorously to create a homogenous solution. The absorbance of each sample was measured in a spectrophotometer at a wavelength of 595 nm. The protein concentration of each sample was determined using a standard curve which was plotted by measuring absorbance at 595 nm of known concentrations of bovine serum albumin using the Bradford assay.

For western blot analysis equivalent amount of protein were loaded onto an SDS-PAGE and resolved by electrophoresis at 125V for 1.5 hours. Subsequently, proteins were electroblotted onto a nitrocellulose or PVDF membranes and subjected to Western blot procedures having the following steps: blocking, incubation with primary antibody/ies, washings, incubation with horseradish peroxidase conjugated-secondary antibody, washing again and finally reaction with chemiluminescence substrate and signal detection.

Example 11: Selection of a Cell Line that Continuously Expresses the Influenza M1 and M2 Proteins MDCK and CHO cells were transfected by electroporation with a linearized DNA vector carrying the M1 and M2 influenza genes. Following selection with hygromycin, single cell clones were isolated using fluorescence-activated cell sorting (FACS) after labeling the cells with combination of antibodies; first as primary an anti-M2 mouse monoclonal antibody which reacted the M2 protein expressed on the cell surface, followed by a flourescein conjugated anti-mouse as secondary.

Sorted single cells were expanded and expression of M1 and M2 proteins was further assessed by Western blot. Cells were lysed, loaded onto and SDS-PAGE (10-20%) and separated by electrophoresis. The proteins were transferred to a PVDF membrane and blocked with 4% skim milk for 1 hour. The membrane was then incubated overnight with a mouse monoclonal anti-M1 protein (1:40,000 dilution) and a mouse monoclonal anti-M2 protein (1:1000 dilution) (Abcam, clone 14C2). The membrane was washed 3× for 5 minutes with 1× TBST and then incubated for 1 hour with horseradish peroxidase conjugated goat anti-mouse IgG (1:50,000 dilution in 2% skim milk) (Thermo Scientific, Rockford, Ill.). The membrane was washed 3× for 10 minutes with 1× TBST followed by 5 minute incubation with SuperSignal West Pico chemiluminescent substrate (Thermo Scientific, Rockford, Ill.). The membrane was exposed to HyBlot CL autoradiography film (Denville Scientific, Metuchen, N.J.).

Figure 9B:
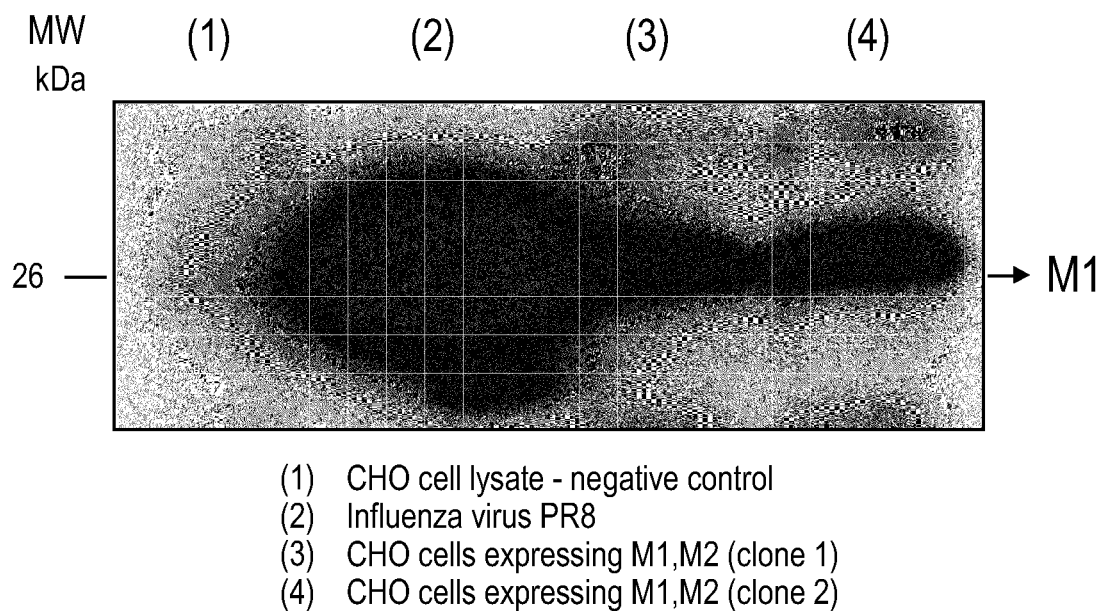

As shown in FIG. 9A lane 3, the MDCK cell lysate produced two major bands which correspond to the M1 protein molecular weight (MW) of ~27 kDA and M2 protein with a MW of ~11 kDA, whereas untransfected control did not show the presence of these proteins. Lane 1: protein marker, lane 2: MDCK cells not expressing influenza M1 and M2 proteins (negative control), lane 3: MDCK cells constitutively expressing influenza A M1 and M2 proteins. Similar results were obtained with the same plasmid was introduced into CHO cells as shown in FIG. 9B and VERO cells.

Example 12: Expression of Remodeled HA/NA Protein in M1/M2 Producing Cells

Transfection of a DNA vector carrying the remodeled HA molecules (FIG. 6 panel I-HA/NA) with or without NA and together with the M1/M2 DNA vector (FIG. 1—panel I-M1/M2) or into cells already expressing the M1/M2 led to the expression of these proteins which were not only present in cell lysates but also in the cell supernatant and concentrated purified supernatant.

Western blot analysis of these samples are shown in FIG. 10 and show production of M1, M2 and HA protein in the transfected cells.

Example 13: Examination of Influenza VLP by Negative Staining Electron Microscopy The supernatant of the transfected cells was subjected to ultra-centrifugation at 200,000×g for 1.5 hours at 4° C. The pellet from the ultra-centrifugation was re-suspended in PBS and 20 μl of the re-suspended pellet was set aside for electron microscopy. This 20 μl sample was fixed with 4% para-formaldehyde and then 5 μl of the fixed material was applied to a 200 mesh carbon coated grid (EMS, Hatfield, Pa.) and allowed to cover the grid for 5 minutes and then washed with water three times. Following this the coated grids were exposed to five drops of 2% uranyl acetate in quick succession to prevent over-staining of the grid with uranyl acetate. Excessive solution was blotted from the grid and then air dried before loading it onto a JOEL JEM 100CX Transmission Electron Microscope. The samples were observed at a magnification of 60,000× to 100,000×.

Figure 11:
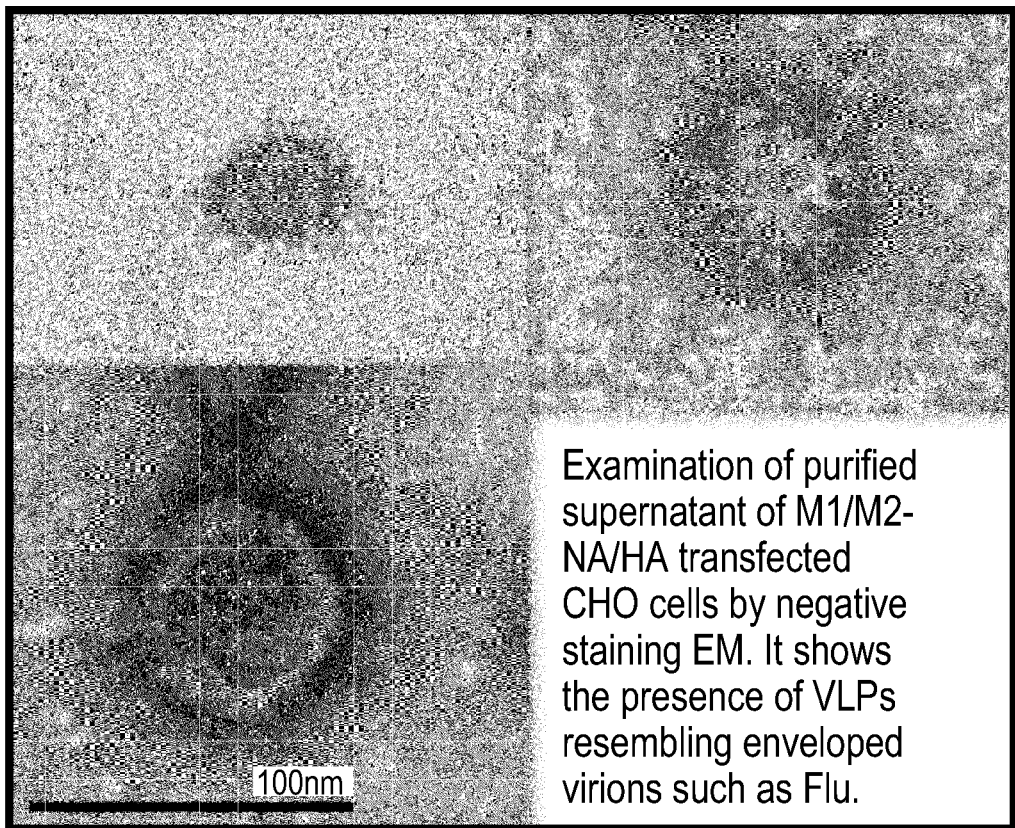

FIG. 11 shows images obtained from purified supernatant of M1/M2-HA/NA CHO cells

What is claimed is:

1. A virus-like particle (VLP) comprising:
at least one influenza matrix protein; and
an antigenic influenza HA polypeptide displayed on the surface of the VLP, the HA polypeptide comprising an $HA_1$ polypeptide and an $HA_2$ polypeptide, the $HA_2$ polypeptide having an extracellular domain, a transmembrane domain and a cytoplasmic domain, the extracellular domain of the $HA_2$ polypeptide comprising at least 173 amino acid residues, and wherein the $HA_1$ polypeptide consists of residues 17-65 and 241 to 346 of the $HA_1$ polypeptide, as numbered relative to wild-type $HA_1$ as set forth by SEQ ID NO:13.

2. The VLP of claim 1, wherein at least one proteolytic cleavage site or at least one linker is inserted into the influenza HA polypeptide.

3. The VLP of claim 1, wherein the transmembrane domain of the influenza $HA_2$ polypeptide is replaced with an HA transmembrane domain from a different strain or subtype than the influenza $HA_2$ polypeptide.

4. The VLP of claim 1, wherein the cytoplasmic domain of the influenza $HA_2$ polypeptide is replaced with an HA cytoplasmic domain from a different strain or subtype than the influenza $HA_2$ polypeptide.

5. The VLP of claim 1, further comprising additional influenza proteins.

6. The VLP of claim 5, wherein the additional influenza protein are selected from the group consisting of one or more wild-type matrix proteins, one or more mutant matrix proteins, one or more hybrid matrix proteins, one or more mutant and hybrid matrix proteins one or more wild-type antigenic glycoproteins, one or more modified antigenic glycoproteins, one or more hybrid antigenic glycoproteins, one or more modified and hybrid antigenic glycoproteins, one or more nucleoproteins (NPs), one or more PB1 proteins, one or more PB2 proteins, one or more PA proteins and combinations thereof.

7. The VLP of claim 1, wherein the VLP is expressed in a eukaryotic cell under conditions which permit the assembly and release of VLPs.

8. The VLP of claim 7, wherein the eukaryotic cell is selected from the group consisting of a yeast cell, an insect cell, an amphibian cell, an avian cell, a plant cell, and a mammalian cell.

9. A method of producing a VLP according to claim 1, the method comprising the steps of transfecting one or more vectors encoding at least one matrix protein and at least one modified influenza HA polypeptide into a suitable host cell and expressing the combination of protein under conditions that allow VLP formation.

10. The method of claim 9, wherein at least one matrix protein is selected from the group consisting of an influenza M1 protein, a thogoto matrix protein and an RSV matrix protein.

11. The method of claim 9, wherein at least one vector further comprises a sequence encoding an influenza M2 protein.

12. The method of claim 9, wherein the one or more vectors are stably transfected into the host cell.

13. The method of claim 9, wherein the at least one matrix protein and the modified influenza HA polypeptide are encoded on separate vectors and further wherein the vector encoding the at least one matrix protein is stably transfected into the cell prior to transfection with the vector encoding the modified influenza HA polypeptide protein.

14. The method of claim 9, wherein the cell is a eukaryotic cell selected from the group consisting of a yeast cell, an insect cell, an amphibian cell, an avian cell, a plant cell, and a mammalian cell.

15. An immunogenic composition comprising at least one VLP according to claim 1.

16. The immunogenic composition of claim 15, further comprising an adjuvant.

17. The immunogenic composition of claim 15, wherein the composition comprises at least two VLPs comprising different influenza HA polypeptides.

18. A method of generating an immune response to influenza in a subject, the method comprising administering to the subject an effective amount of the immunogenic composition according to claim 15.

19. The method of claim 18, wherein the composition is administered mucosally, intradermally, subcutaneously, intramuscularly, or orally.

20. The method of claim 18, wherein the immune response vaccinates the subject against multiple strains or subtypes of influenza.

21. The method of claim 18, wherein the subject is a human.

* * * * *